United States Patent
Yang

(10) Patent No.: US 9,696,444 B2
(45) Date of Patent: *Jul. 4, 2017

(54) DYNAMIC THRESHOLD SYSTEMS, COMPUTER READABLE MEDIUM, AND PROGRAM CODE FOR FILTERING NOISE AND RESTORING ATTENUATED HIGH-FREQUENCY COMPONENTS OF ACOUSTIC SIGNALS

(71) Applicant: Saudi Arabian Oil Company, Dhahran (SA)

(72) Inventor: Yunlai Yang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 379 days.

This patent is subject to a terminal disclaimer.

(21) Appl. No.: 14/485,613

(22) Filed: Sep. 12, 2014

(65) Prior Publication Data

US 2015/0071036 A1 Mar. 12, 2015

Related U.S. Application Data

(60) Provisional application No. 61/877,117, filed on Sep. 12, 2013.

(51) Int. Cl.
*G01V 1/00* (2006.01)
*G01V 1/36* (2006.01)
(Continued)

(52) U.S. Cl.
CPC ............ *G01V 1/364* (2013.01); *G01N 29/11* (2013.01); *G01N 29/32* (2013.01);
(Continued)

(58) Field of Classification Search
CPC .... G01N 29/11; G01N 29/32; G10L 21/0208; G10L 21/0232; G10L 2021/02163;
(Continued)

(56) References Cited

U.S. PATENT DOCUMENTS 4,875,166 A * 10/1989 Carroll ............... G01V 1/364
   367/44
5,133,013 A * 7/1992 Munday ............ G10L 21/0208
   704/226
(Continued)

FOREIGN PATENT DOCUMENTS

GB 2426167 A 11/2006

OTHER PUBLICATIONS

Drumheller, D. "Attenuation of sound waves in drill strings" The Journal of the Acoustical Society of America, vol. 94, No. 4, Woodbury, NY, Oct. 1993, pp. 2387-2396, XP000412921.
(Continued)

*Primary Examiner* — Krystine Breier
(74) *Attorney, Agent, or Firm* — Bracewell LLP; Constance G. Rhebergen; Christopher L. Drymalla

(57) ABSTRACT

Systems, computer readable media, and program code to provide for filtering noise and/or restoring attenuated spectral components in acoustic signals, are provided. An exemplary embodiment of a system is configured for dynamically filtering each of a plurality of raw FFT data samples of a record to remove or attenuate background noise contained therein to thereby produce a corresponding plurality of cleaned FFT data samples. The sample-specific background noise is removed or attenuated by a record-specific dynamic filter to produce the corresponding cleaned FFT data samples. The system can also perform the operations of restoring the attenuated high-frequency components of the cleaned data samples through application of a record-specific Restoring Processor at least partially defined by a portion of the cleaned data samples and a Gain Function to thereby produce cleaned and restored data samples, and applying an inverse transformation to convert the cleaned
(Continued)

and restored data samples into cleaned and restored data samples in time domain data.

28 Claims, 19 Drawing Sheets

(51) Int. Cl.
*G01N 29/11* (2006.01)
*G10L 21/0208* (2013.01)
*G01N 29/32* (2006.01)
*G01V 1/40* (2006.01)
*G10L 21/0216* (2013.01)
*G10L 21/0232* (2013.01)

(52) U.S. Cl.
CPC ............ *G10L 21/0208* (2013.01); *G01V 1/40* (2013.01); *G01V 2210/324* (2013.01); *G01V 2210/40* (2013.01); *G10L 21/0232* (2013.01); *G10L 2021/02163* (2013.01)

(58) Field of Classification Search
CPC ...... G01V 1/364; G01V 1/40; G01V 2210/40; G01V 2210/324
See application file for complete search history.

(56) References Cited

U.S. PATENT DOCUMENTS

| | | | |
|---|---|---|---|
| 6,138,093 A * | 10/2000 | Ekudden | ................ G10L 19/26 704/205 |
| 6,415,253 B1 | 7/2002 | Johnson | |
| 6,801,889 B2 | 10/2004 | Walker | |
| 7,742,914 B2 | 6/2010 | Kosek | |
| 7,881,479 B2 | 2/2011 | Asada | |
| 8,438,026 B2 | 5/2013 | Fischer | |
| 2001/0028713 A1 | 10/2001 | Walker | |
| 2004/0122596 A1 | 6/2004 | Sudhakar | |
| 2005/0071156 A1 | 3/2005 | Xu et al. | |
| 2006/0200344 A1 | 9/2006 | Kosek | |
| 2007/0025560 A1 | 2/2007 | Asada | |
| 2008/0215322 A1 | 9/2008 | Fischer | |
| 2009/0281800 A1 | 11/2009 | LeBlanc | |
| 2009/0281801 A1 | 11/2009 | Thyssen | |
| 2009/0281802 A1 | 11/2009 | Thyssen | |
| 2009/0281805 A1 | 11/2009 | LeBlanc | |
| 2009/0287496 A1 | 11/2009 | Thyssen | |
| 2012/0143604 A1 | 6/2012 | Singh | |
| 2013/0194893 A1* | 8/2013 | Nagarajappa | .......... G01V 1/364 367/43 |
| 2015/0071035 A1* | 3/2015 | Yang | ..................... G01V 1/364 367/25 |

OTHER PUBLICATIONS

Evans et al. "Time-Frequency Quantile-Based Noise Estimation" Proceedings of EUSIPCO, vol. 1, Jan. 1, 2002, 4 pages, XP055156425.

International Search Report and Written Opinion for PCT/US2014/055516 (SA5191PCT) dated Dec. 10, 2014.

Pham et al. "Robust Speech Recognition Using Adaptive Noise Threshold Estimation and Wavelet Shrinkage" IEEE, Communications and Electronics, Second International Conference on ICCE, Piscataway, NJ, Jun. 4, 2008, pp. 206-211, XP031291473.

S. Boll, Suppression of Acoustic Noise in Speech Using Spectral Subtraction, IEEE Transactions on Acoustics, Speech, and Signal Processing, vol. ASSP-27, No. 2, Apr. 1979.

* cited by examiner

Sample 3A

DYNAMIC THRESHOLD SYSTEMS, COMPUTER READABLE MEDIUM, AND PROGRAM CODE FOR FILTERING NOISE AND RESTORING ATTENUATED HIGH-FREQUENCY COMPONENTS OF ACOUSTIC SIGNALS

RELATED APPLICATIONS

This application is a non-provisional of and claims priority to and the benefit of U.S. Provisional Application No. 61/877,117, filed on Sep. 12, 2013, titled "Dynamic Threshold Methods, Systems, and Program Code for Filtering Noise and Restoring Attenuated High-Frequency Components of Acoustic Signals," and PCT Application PCT/US2014/55516, titled "Dynamic Threshold Methods, Systems, Computer Readable Media, and Program Code For Filtering Noise and Restoring Attenuated High-Frequency Components of Acoustic Signals, filed on Sep. 12, 2014, and is related to U.S. Non-Provisional patent application Ser. No. 14/485,562, titled "Dynamic Threshold Methods For Filtering Noise and Restoring Attenuated High-Frequency Components of Acoustic Signals, filed on Sep. 12, 2014, each incorporated herein by reference in their entirety.

BACKGROUND OF THE INVENTION

Field of the Invention

The invention relates generally to the field of signal processing. More specifically, the invention is related to methods, systems, and program code for filtering noise and restoring attenuated spectral components in signals.

Description of the Related Art

Signals in the form of acoustic wave (acoustic signals), for example, generated by an acoustic wave source can travel through various materials including reservoir and non-reservoir rock, well tubulars including drilling pipe, and other drilling equipment including the drilling bit. Acoustic signals generally lose their accuracy due to the accompanied background noise during transmission and recording. The background noise is composed of two parts, an internal part which is generated from the measurement system, and an external part which comes from the surround environment.

Acoustic signals may also be distorted during transmission and recording due to the attenuation of the signal, particularly the high frequency components. Attenuation of the amplitude spectrum of an acoustic signal is generally non-uniform. The higher the frequency of the spectral components of the acoustic signals, the greater the attenuation of the respective spectral components of the acoustic signals.

As illustrated in FIG. 1A, both background noise and the non-uniform attenuation will combined together to deteriorate the quality of the acoustic signals. FIG. 1A shows an acoustic signal 21 recorded simultaneously using a microphone and an accelerometer. The frequency components 22 of a sample recorded by the accelerometer represent an un-attenuated version of frequency components of the sample of the audio signal; i.e., what they should have been but for the attenuation. It can be seen here that the high-frequency components of the acoustic signal 21 recorded by the microphone are attenuated down to the level of noise.

To increase the quality of the signals, the deteriorated signals should be filtered to remove noise and their attenuated spectral components should be restored. There are two common approaches: frequency filtering and amplitude filtering. Frequency filtering is to remove from a signal some unwanted frequency components by using an electronic device or a mathematical process. In this approach, any frequency components with frequency greater and/or less than preselected cutoff values are removed or heavily attenuated.

When a mathematical process employed, signals in time domain (e.g., graphically illustrated as signal amplitude over time) are converted to the frequency domain to represent the signals in the amplitude spectrum. This is accomplished, for example, through use of the Fast Fourier Transformation (FFT). FIG. 1A illustrates an example of a pair of acoustic signals, existing in the time domain, being converted into the frequency domain. With the signal converted into the frequency domain, the signal components in the amplitude spectrum having a frequency above and/or below a cutoff value are removed.

Amplitude filtering is normally a mathematical process in which components in the amplitude spectrum with an amplitude above and/or below a cutoff (threshold) value are removed. If required, an inverse FFT is then performed on the filtered frequency domain signal to recover the time domain output signal.

In these two approaches, proper cutoff (threshold) values are critical. It is not always the case, however, that there exist clear cutoffs usable to separate the acoustic signals from the noise. FIG. 1B illustrates an example of a restored signal (solid line) where the amplitude cutoff threshold was too low, which resulted in excessive filtering. FIG. 1C illustrates an example of a restored signal (solid line) where the amplitude cutoff was too high, which resulted in excessive noise remaining and amplified in the restored signal.

Some relatively sophisticated techniques have been proposed to filter noise by using "Spectral Subtraction" methodology, e.g. S. F. Boll: "Suppression of Acoustic Noise in Speech Using Spectral Subtraction", IEEE Trans. on Acous. Speech and Sig. Proc., 27, 1979. pp. 113-120; and U.S. patent 2007/0255560 A1, titled "Low Complexity Noise Reduction Method". In this type of approach, the noisy signals are filtered by subtracting the spectral noise bias. In the first example, the spectral noise is calculated during non-speech activity. In the second example, the spectral noise is estimated from a "Noisy Activity Detector" procedure. This type of approach, however, would be difficult to apply to situations in which the noise properties are unknown, such as, for example, those associated with drilling operations, to include drilling operations involving real-time steering of the drilling bit.

To further increase the accuracy of acoustic signals, the attenuated spectral components should be restored. U.S. patent 2012/0143604 A1, titled "Method for Restoring Spectral Components in Denoised Speech Signals," discusses an approach for doing so. This approach, however, requires training undistorted bases obtained from a full-bandwidth clean speech signal. This requirement, therefore, limits the application of the approach to scenarios in which such a full-bandwidth clean signal is available, excluding application of the approach from those scenarios where the full-bandwidth cannot be obtained. U.S. Patent 2004/0122596 A1, "Method for High Frequency Restoration of Seismic Data," describes an approach in which attenuation of high frequency components is estimated from acoustic signals reflected at consecutive depth levels of formation boundaries. An inverse operator is then determined from the attenuation for each depth level. The determined inverse operators are applied to reflected acoustic signals to restore their attenuated high frequency components. This approach, however, requires knowing the manner in which the high frequency components attenuate.

Each of above mentioned methods or approaches have their merits and specialized area of application. Recognized by the inventor, however, is that there are numerous situations in which acoustic signals cannot be separated from the accompanied noise by some frequency or constant amplitude cutoffs, or clean signal or noise samples, and where the pattern of high frequency component attenuation cannot be obtained.

As noted above, acoustic signals can attenuate during transmission and recording. Under various conditions, some or all of high frequency components of the signals can attenuate to the similar level as background noise. For example, the virgin acoustic (sound) signal generated from an underwater device is both distorted by substantial accompanied background noise that varies with time, and is distorted as a result of attenuation of its high frequency components during transmission through the water. When recorded from a long distance away from the source, the recorded sound will have inherent noise and the sound will be significantly distorted due to the attenuated high frequency components.

Recognized by the inventor is that the situations are similar when recording acoustic signals from a source in distance in air or from underground. Accordingly, the inventor has recognized that common characteristics of these situations include: (1) the background noise may not be constant, and (2) the high frequency components generally will have attenuated significantly by the time the signal reaches to the recording devices. Correspondingly, the inventor has recognized that there exists a need for systems, computer programs, computer readable media, and computer assisted methods to both filter non-constant noise, and then to restore attenuated high frequency components of the filtered signals sufficient to provide a filtered and restored signal, substantially matching the original virgin signal.

SUMMARY OF THE INVENTION

In view of the foregoing, various embodiments of the invention advantageously provide methods, systems, computer readable media, and program code for filtering noise and restoring attenuated spectral components in signals. Various embodiments of the invention, as a result of a capability of filtering and restoring acoustic signals sufficient to provide a signal of sufficient quality to allow "listening" to the drilling bit. According to various embodiments, the drill bit sound can also be used to derive petrophysical properties in real time during drilling, and/or to allow real-time steering of drilling bit.

The recorded sound signals include background noises and their high-frequency components are attenuated. Various embodiments of the invention advantageously provide enhanced methodologies to filter the background noise and to restore the attenuated high frequency components of the signals, to thereby retrieve more information from the signals. Further, various embodiments can advantageously be applied to seismic data processes to enhance the quality of the seismic signals, among other uses.

More specifically, an example of an embodiment of a system of filtering noise and restoring attenuated spectral components in signals and computer readable medium, can perform the operations of receiving acoustic signals for a preselected time duration to form one or more records of acoustic signals (typically in the time domain), and/or performing one or more of the following operations for each of at least one, but more typically a plurality of acoustic signal records, each separately recorded for a relatively short time period. The operations can also or alternatively include sampling the acoustic signals within the respective record, e.g., by a preprocessor, to thereby form sampled digitized data containing a plurality of raw data samples, for example, if not already accomplished. The operations can also or alternatively include applying a Fast Fourier Transform to convert the plurality of raw data samples into a plurality of raw FFT data samples. The raw FFT data samples are composed of acoustic signal data and background noise.

The operations can also include dynamically filtering each of the plurality of raw FFT data samples to remove or attenuate sample-specific background noise contained therein to thereby produce a corresponding plurality of cleaned FFT data samples. The sample-specific background noise is removed or attenuated by a tuned record-specific dynamic filter to produce the corresponding cleaned FFT data samples. The tuned dynamic filter is at least partially defined by the selected dynamic amplitude noise cutoff applied to each of the plurality of raw FFT data samples. The selected dynamic amplitude noise cutoff is defined by a selected value of the record-specific base noise percentile and a selected record-specific value of the threshold parameter. The cleaned FFT data samples can include the acoustic signal data having substantially attenuated high-frequency components.

The operations can also include restoring the attenuated high-frequency components of the cleaned data samples to thereby produce cleaned and restored data samples being in the frequency domain. The operation of restoring can be performed through application of a record-specific Restoring Processor at least partially defined by a portion of the cleaned data samples and a Gain Function. The operations can also include applying an inverse transformation to convert the cleaned and restored data samples into cleaned and restored data samples in time domain data.

The operations can also or alternatively include first tuning an initial record-specific dynamic filter at least partially defined by an initial Dynamic Amplitude Noise Cut off defined by an initial record-specific Base Noise Percentile and an initial record-specific value of a Threshold Parameter in order to form a tuned (selected) dynamic filter to perform the above filtering operation. The tuning of the initial dynamic filter can include determining the initial record-specific Base Noise Percentile defined as a $K^{th}$ percentile within a record-specific Specific Frequency Range of an amplitude spectrum of each of the plurality of samples of a respective record, below which each frequency component within the Specific Frequency Range of the respective amplitude spectrum of each of the plurality of samples within the respective record is treated as background noise with substantial certainty. This "noise floor" is the level of background noise in a signal, or the level of noise introduced by the system, below which the signal that's being captured cannot be isolated from the noise.

This tuning operation can also include determining the initial record-specific value for the threshold parameter defined as either a threshold factor to be multiplied with the initial record-specific base noise percentile or a threshold elevator to be added to the initial record-specific base noise percentile to determine a value for a selected dynamic amplitude noise cutoff to be applied separately to each of the plurality of raw data samples.

The tuning operation includes the operations of receiving or retrieving a subset of the plurality of samples of each respective record of the one or more records. If the respective record is a recorded record, the tuning operation can include retrieving a subset of the plurality of raw data samples recorded at substantially different times with different background noise levels to thereby define a set of Representative FFT Data samples. If the respective record is alternatively an online record to be processed and the raw data samples cannot be selected at substantially different times, the tuning operation includes receiving a subset of the plurality of raw data samples at a beginning of the respective record to thereby define the set of Representative FFT Data samples.

Regardless, the tuning operation can also include selecting a Specific Frequency Range for a respective record of the one or more records. The Specific Frequency Range can be defined by a range of frequencies common to each sample of a set of Representative FFT Data samples containing frequency components being dominated by background noise, or if no range of frequencies is dominated by background noise, a range of frequencies common to each of the samples of the set of Representative FFT data samples containing a higher percentage of background noise than other substantial ranges of consecutive frequencies of the set of Representative FFT data samples.

The tuning operation can also include selecting an initial Base Noise Percentile for the respective record of the one or more records. This selecting operation can include: identifying an apparent dividing amplitude under which at least approximately all of the frequency components within the selected Specific Frequency Range are background noise for each of the samples within the set of Representative FFT Data samples, selecting an initial value of the record-specific Threshold Parameter for the respective record, and determining the Dynamic Amplitude Noise Cutoff for the respective record defined by the selected Base Noise Percentile and the selected record-specific value of the Threshold Parameter. The tuning operation can also include evaluating results of the initial Dynamic Filter at least partially defined by the Dynamic Amplitude Noise Cutoff, on one or more samples within a set of Representative data samples extracted from the plurality of raw data samples to thereby construct the tuned dynamic filter.

The operation of evaluating the initial Dynamic Filter on one or more samples within the set of Representative FFT data samples, can include graphically evaluating an amplitude location of the Dynamic Amplitude Noise Cutoff of one or more of the samples within the set of Representative FFT data samples, and/or evaluating results of an initial Dynamic Filter at least partially defined by the initial Dynamic Amplitude Noise Cutoff, on one or more samples within the set of Representative FFT data samples. This operation can include determining the initial Dynamic Filter, performing initial dynamic filtering of the one or more samples within the set of Representative FFT data to thereby produce a corresponding one or more Cleaned FFT data samples, and directly graphically examining the one or more Cleaned FFT data samples by comparing each respective cleaned FFT data sample to its corresponding raw FFT data sample.

The operation of evaluating results of an initial Dynamic Filter on one or more samples within the set of Representative FFT data samples, can also or alternatively include determining the initial Dynamic Filter, performing initial dynamic filtering of the one or more samples within the set of Representative FFT data to thereby produce a corresponding one or more Cleaned FFT data samples, and examining one or more time domain data samples corresponding to the one or more cleaned FFT data samples. This operation can include performing an inverse FFT on the one or more cleaned FFT data samples to thereby transform the cleaned FFT data into time domain format to thereby produce the one or more time domain data samples, and producing sounds corresponding to the one or more time domain data samples using a listening device.

If the results of the initial Dynamic Filter are not acceptable, the operations can include repeating the operations of adjusting the Threshold Factor to thereby shift the Dynamic Amplitude Noise Cutoff in a corrective direction and evaluating results of an adjusted initial Dynamic Filter, until acceptable. If the results of the evaluation of the initial Dynamic Filter are acceptable, the operations can also include evaluating the initial Dynamic Filter on a second set of Representative FFT data samples.

If the cleaned FFT data samples are stored such that a subset of the plurality of the cleaned FFT data samples can be selected at substantially different time intervals, the operations can also or alternatively include performing the operation of retrieving a subset of the plurality of Cleaned FFT data samples representing samples of signals recorded at substantially different times with probable different background noise levels to thereby define a set of Representative Cleaned FFT Data samples used in building or selecting the gain function and forming the record-specific Restoring Processor. If the cleaned FFT data samples are operation streamed online such that a subset of the plurality of the cleaned FFT data samples cannot be selected at substantially different time intervals, the operations can also or alternatively include performing the operation of receiving a subset of the plurality of Cleaned FFT data samples at a beginning of the respective record to thereby define the set of Representative Cleaned FFT Data samples used in building or selecting the gain function and forming the Restoring Processor.

According to one or more embodiments of a system and/or program product, the record-specific Restoring Processor is an operational record-specific Restoring Processor. According to this embodiment, the operations can include selecting an initial Restoring Processor for the respective record of the one or more records. This operation can include selecting a set of Representative Cleaned FFT data samples from the plurality of cleaned FFT data samples, building or selecting the gain function or selecting the gain function from a database responsive to the Representative Cleaned FFT data samples, adjusting parameters of the gain function to thereby form an initial Restoring Processor, performing initial restoration processing of the one or more samples within the set of Representative Cleaned FFT data samples by the initial Restoring Processor at least partially defined by the gain function, to thereby produce a corresponding one or more restored samples within a set of Restored FFT data samples, and evaluating the initial Restoring Processor.

If the results of the initial Restoring Processor are not acceptable, the operations can include repeating the operations of building or selecting a new gain function, adjusting parameters of the gain function, and evaluating results of the initial Restoring Processor, until acceptable. If the results of the evaluation of the initial Restoring Processor are acceptable, the operations can include evaluating the initial Restoring Processor on a second subset of the plurality of Cleaned FFT data samples. The operation of evaluating the initial Restoring Processor can include graphically comparing each sample of the set of Restored FFT data samples with its correspondent Cleaned FFT data sample, and/or examining one or more time domain data samples corresponding to one or more samples of the set of Restored FFT data samples. This operation can include performing an inverse FFT on the one or more Restored FFT data samples to thereby transform the Restored FFT data into time domain format to thereby produce the one or more time domain data samples, and producing sounds corresponding to the one or more time domain data samples using a listening device.

Advantageously, one or more embodiments of the present invention can also include a system of filtering noise and restoring attenuated spectral components in acoustic signals, configured to execute operations defined by one or more combinations of one or more of the operations, described above. The system can include a dynamic noise filtering and signal restoration computer having one or more processors and memory in communication with the one or more processors; and a dynamic noise filtering and signal restoration program stored in the memory of the dynamic noise filtering and signal restoration computer to provide for filtering noise, restoring attenuated spectral components or both filtering noise and restoring attenuated spectral components in acoustic signals, the program including instructions that when executed by the dynamic noise filtering and signal restoration computer cause the computer to perform operations defined by the computer implementable method steps, described above.

Further advantageously, one or more embodiments can also include one or more embodiments of the method or methods of filtering noise, restoring attenuated spectral components, or both filtering noise and restoring attenuated spectral components in acoustic signals. The method or methods can include method steps comprising one or more combinations of one or more of the operations, described above.

Still further advantageously, one or more embodiments also include a computer program product comprising computer program code stored on a non-transitory computer readable medium to provide for filtering noise, restoring attenuated spectral components, or both filtering noise and restoring attenuated spectral components in acoustic signals. The computer program code can include a set of instructions, that when executed by one or more processors, cause the one or more processors to perform operations defined by one or more combinations of one or more of the operations, described above.

Advantageously, according to one or more embodiments, unlike conventional filtering techniques, these "Dynamic Amplitude Noise Cutoff" techniques allow a best noise cutoff to be evaluated for and then applied to each individual sample. Accordingly, one or more embodiments provide better solutions to filter background noise and/or to restore attenuated components of acoustic signals. One or more embodiments have been applied to a real world project with immediate practical applications. Additionally, one or more embodiments can advantageously be applied to seismic survey in the restoration of attenuated high frequency signals, and thus, can serve to increase the resolution of seismic surveys.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Notation: Two terms, "record" and "sample," are clarified for their specific meaning in this specification. A record (e.g., of acoustic signals) is a set of data recorded or otherwise captured for a certain time period, from the same source located in the same environment. A record can be digitized into serial slices of the data along a time line running within the boundaries of the time period, with each slice being a small part of the record. One slice of the data is called a sample (or frame). Therefore, a digitized record is composed of a series of samples. Additionally, the frequency domain representation of an acoustic signal is called the "amplitude spectrum" or just "spectrum" of the signal. Each sine wave line of the spectrum is called a component of the total signal in a sample.

When acoustic signals are recorded, there are always noises within the recorded signals. The recorded signals may be further deteriorated during transmission and recording by non-uniform attenuation of high frequency components. Signal in the form of acoustic wave will lose its accuracy due to the accompanied background noise and attenuated high frequency components during transmission and recording. Filtering noise can enhance the quality of the signal directly. Filtering is generally a prerequisite step to restoring attenuated high frequency components. A number of denoising methodologies are known. The conventional methodologies typically first transform the acoustic signals from time domain format into frequency domain format, sample-by-sample, attempt to filter or reduce the noise, and then attempt to restore attenuated components. To filter the noise, conventional methodologies typically first identify/estimate the noise, and then reduce the noise using the identified noise, either by subtraction or filtering, or suppression. Various methodologies include utilizing a constant amplitude cutoff for a selected record, a constant frequency cutoff for a selected record, or in special cases, pure noise data such as, for example, pauses between speech during a mobile phone conversation to filter the noise.

Figure 1A:
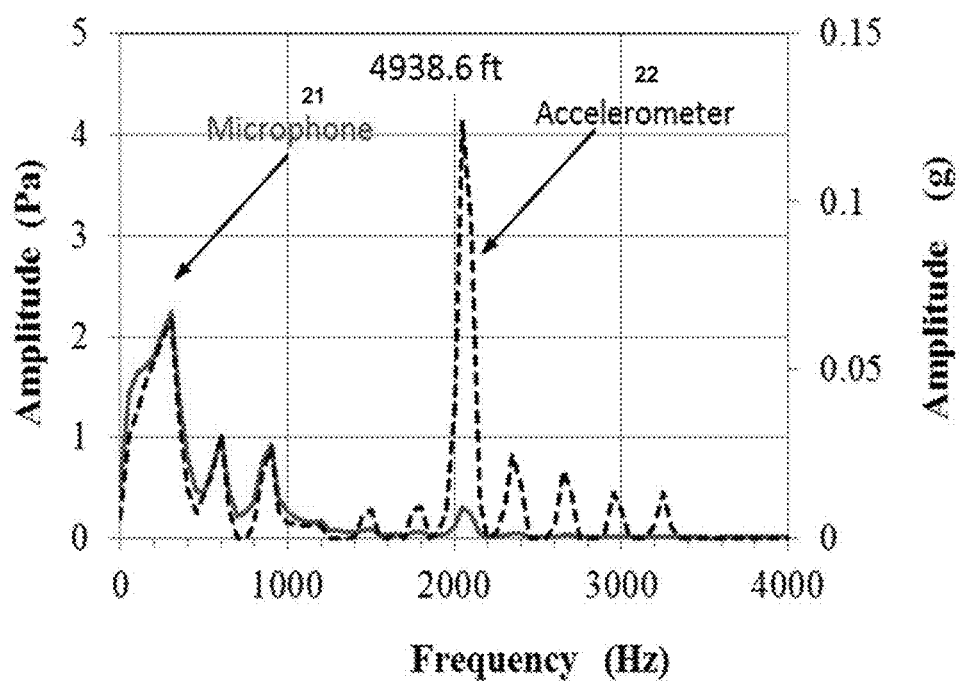
FIG. 1A is a graph providing a comparative example between an audio signal simultaneously recorded by a microphone and by an accelerometer to illustrate attenuation of the audio signal recorded by the microphone.
Figure 1B:
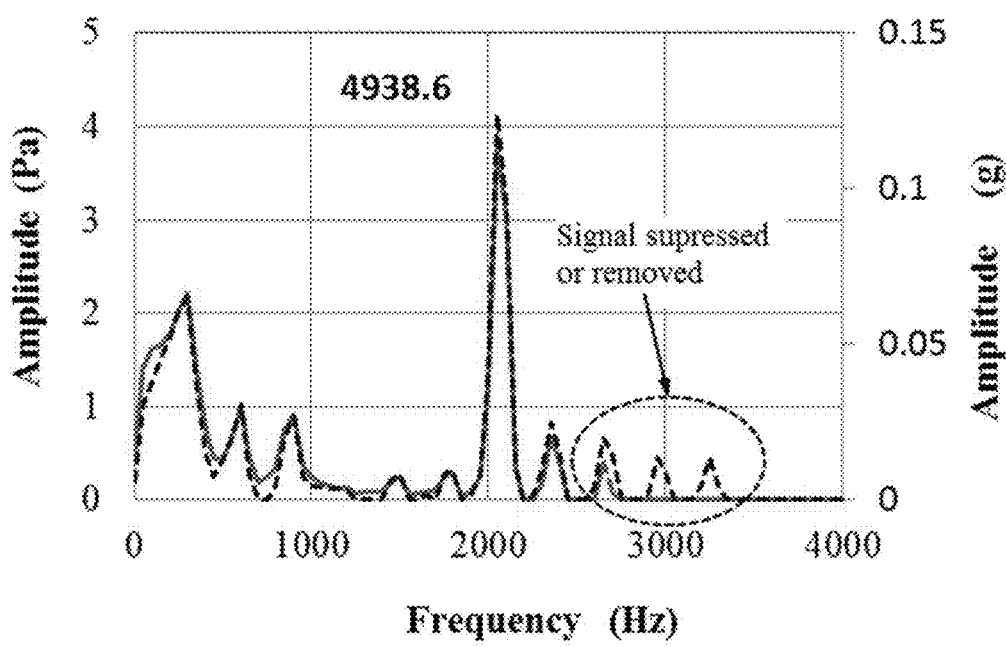
FIG. 1B is a graph illustrating over filtering of high-frequency components.
Figure 1C:
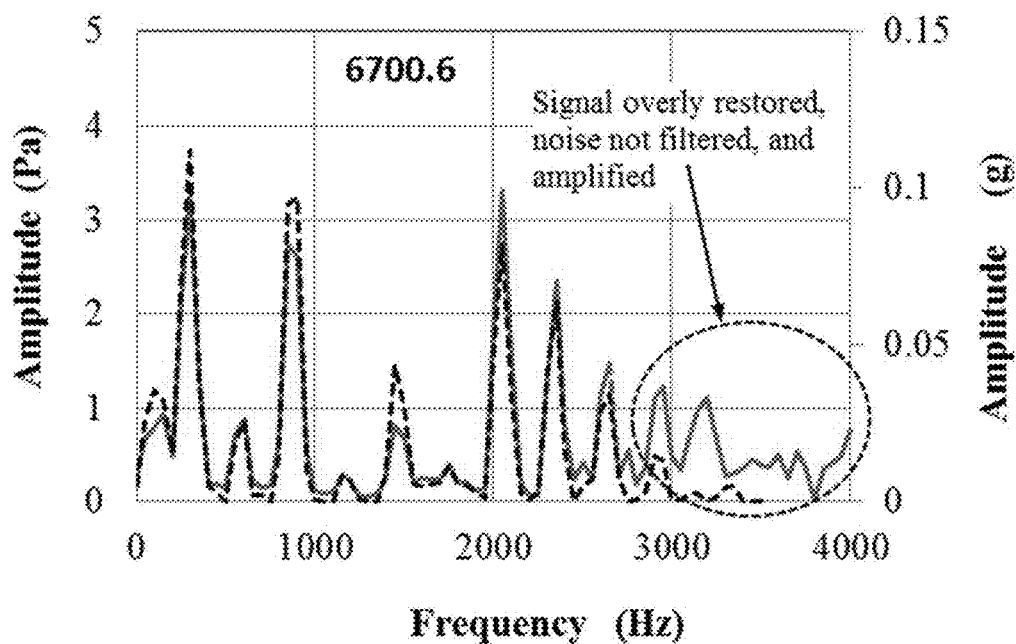
FIG. 1C is a graph illustrating under filtering of high-frequency components.
Figure 1D:
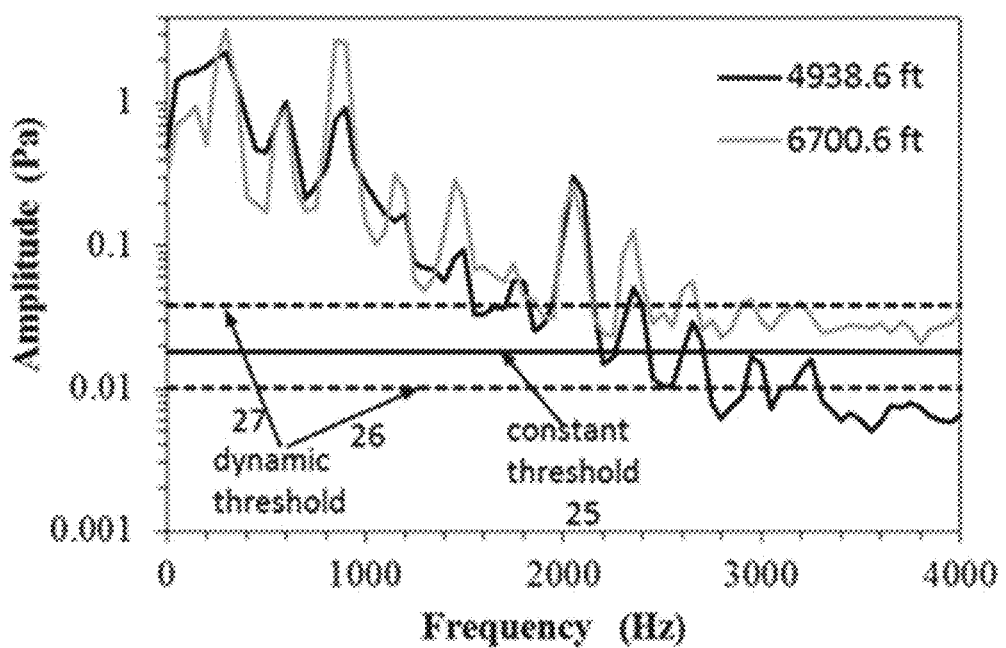
FIG. 1D is a graph illustrating a comparison to a conventional constant threshold amplitude value and dynamic threshold amplitude values according to an embodiment of the invention.

As shown in FIG. 1D illustrating two audio signals, a problem is that acoustic signals may not contain pure noise frames and the background noise may not be filtered by using a constant amplitude or frequency cutoff Another problem is that the noise estimate is usually inexact, especially when the noise is time-varying. As a result, maintaining a constant threshold 25 according to conventional methodologies either results in the excessive removal of signal (see FIG. 1B) or some residual noise remaining after denoising, which can be excessively amplified during restoration (see FIG. 1C).

Figure 1E:
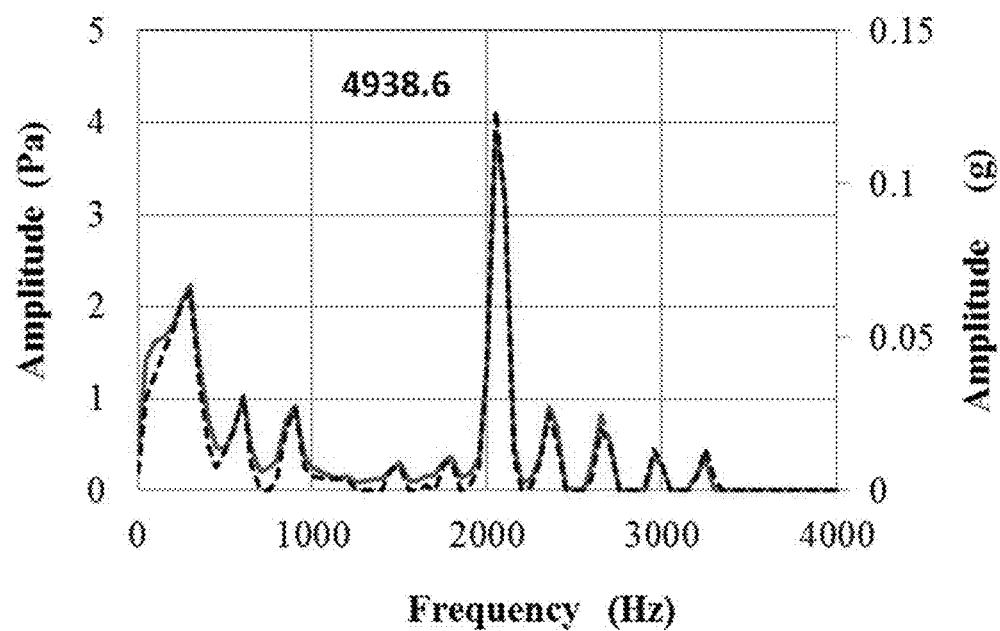
FIGS. 1E-1F are a pair of graphs illustrating the results of signal filtering and restoration of high-frequency components utilizing dynamic threshold amplitude values according to an embodiment of the invention.
Figure 1F:
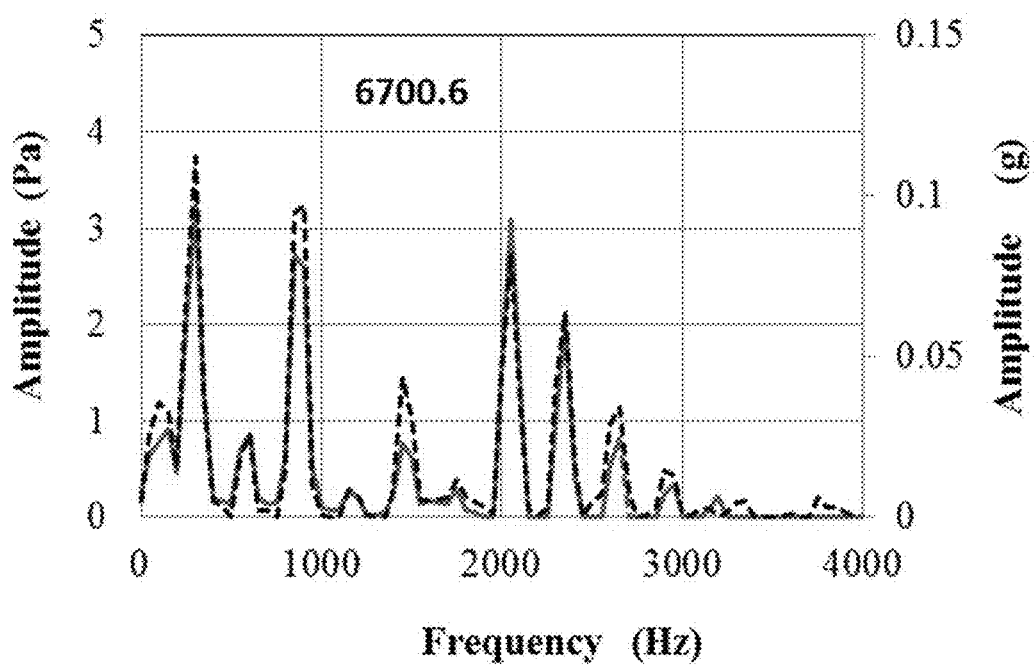

As shown in FIGS. 1A and 1E-1F, various embodiments of the invention can provide both signal filtering and restoration of high-frequency components (shown as solid lines overlaid against an un-attenuated accelerometer signal shown as a dashed line). According to one or more embodiments of the invention, the background noise is filtered by a "Dynamic Threshold" created, decided, or otherwise determined through a process according to one or more embodiments of the invention. Using this process, a specific amplitude noise cutoff is evaluated for each individual sample of a given record and is then applied to the same sample to filter out the background noise of the sample. The attenuated spectral components of the samples are then restored from the filtered or cleaned samples.

Figure 3A:
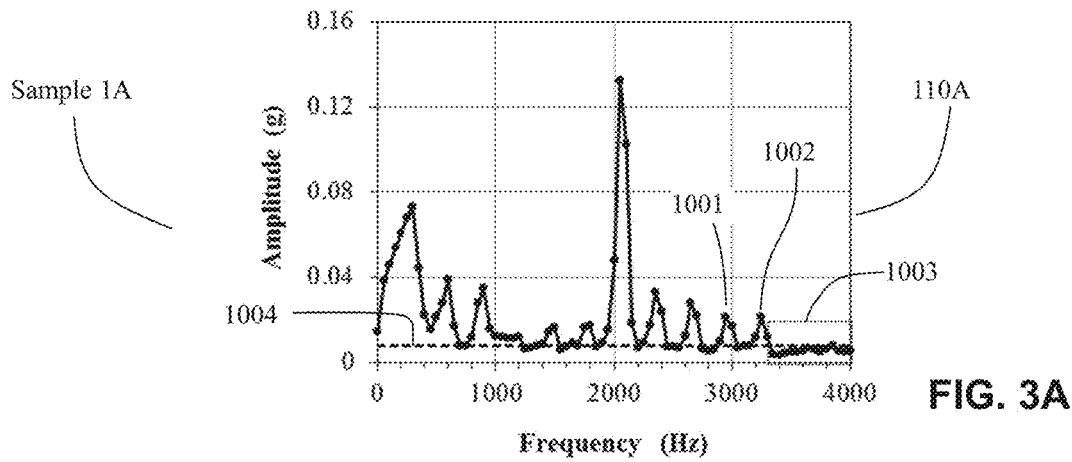
FIGS. 3A-3C are a set of graphs showing the amplitude spectrum of sound sample recorded by an accelerometer and by a microphone.

According to various embodiments of the invention, all obvious peaks on an amplitude spectrum can be treated as parts of the signal and large featureless sections on the amplitude spectrum are treated as background noise. For example, the part encircled by the dotted rectangles on FIGS. 3A and 3C are treated as background noise. As noted above, background noise is typically time varying, i.e. it changes from frame to frame on FFT spectrums. Accordingly, various embodiments of the invention treat background noise as time varying, i.e. background noise is treated changing from frame to frame. Within a frame, i.e. within a FFT spectrum, however, the background noise is treated as constant. That is the background noise for all the data points (within whole frequency range) within a FFT spectrum is considered constant. Various embodiments of the invention provide for evaluation of a Dynamic Amplitude Threshold (cutoff) for each frame signal, i.e. for each FFT sample, based on its background noise features, of a given record. The record is then filtered frame by frame using the cutoff evaluated for the frame. Beneficially, this can provide for evaluating an amplitude cutoff for a frame and then is applied to the same frame.

Figure 2:
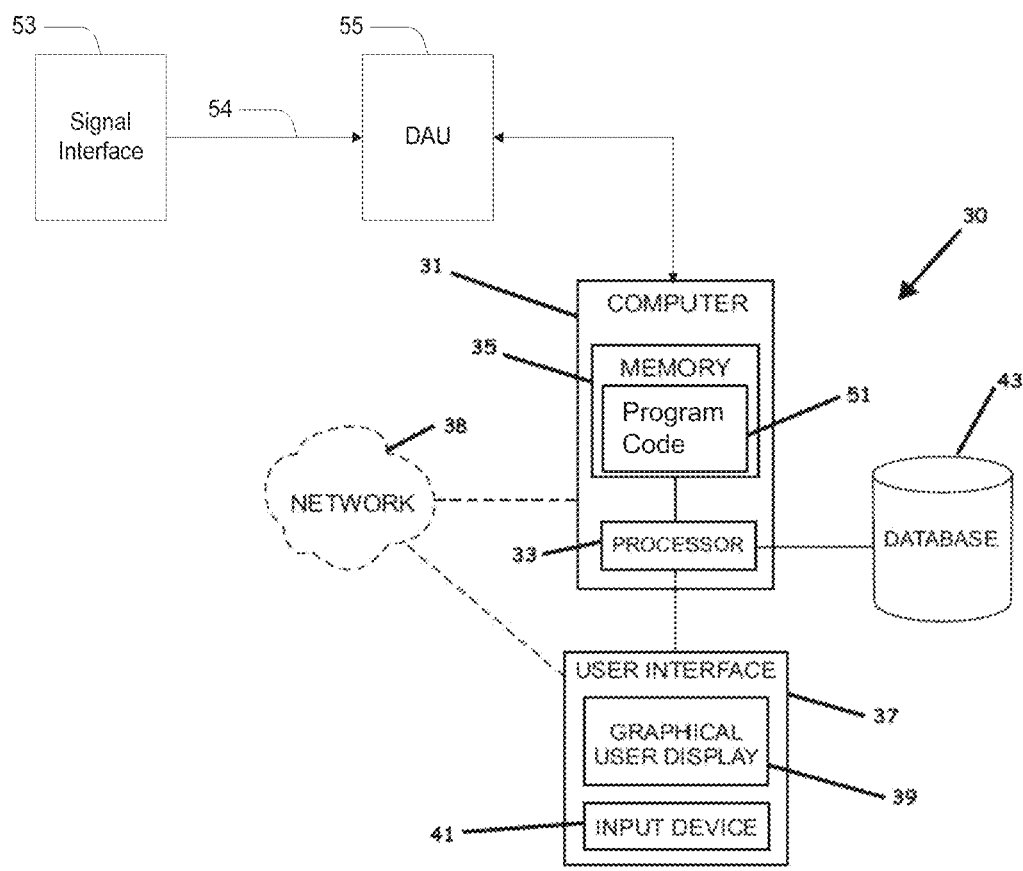
FIG. 2 is a block flow diagram illustrating major system components of a system for providing dynamic noise filtering and attenuated spectral component restoration according to an embodiment of the invention.

FIG. 2 illustrates an example of a system 30 for providing dynamic noise filtering and attenuated spectral component restoration. The system 30 can include a dynamic noise filtering and signal restoration computer 31 having one or more processors 33, memory 35 coupled to the processors 33 to store software and/or database records therein, and optionally a user interface 37 that can include a graphical display 39 for displaying graphical images, and a user input device 41 as known to those skilled in the art, to provide a user access to manipulate the software and database records. Note, the computer 31 can be in the form of a standalone unit, a component of a well instrument, a personal computer, or in the form of a server or multiple servers serving multiple remotely positioned user interfaces 37. Accordingly, the user interface 37 can be either directly connected to the computer 31 or through a network 38 as known to those skilled in the art. The system 30 can also include one or more databases 43 stored in memory (internal or external) that is operably coupled to the dynamic noise filtering and signal restoration computer 31, as would be understood by those skilled in the art. The one or more databases 43 can include a plurality of acoustic wave files recorded, for example, during drilling operations to provide for identifying rock properties in real-time during drilling.

The system 30 can also include dynamic noise filtering and signal restoration computer program 51 provided stand-alone or stored in memory 35 of the dynamic noise filtering and signal restoration computer 31. The dynamic noise filtering and signal restoration computer program 51 can include instructions that when executed by a processor or a computer such as, for example, the dynamic noise filtering and signal restoration computer 31, cause the computer to perform operations to perform dynamic noise filtering and attenuated spectral component restoration in each of multiple samples of multiple acoustic wave signal records or files. Note, the dynamic noise filtering and signal restoration computer program 51 can be in the form of microcode, programs, routines, and symbolic languages that provide a specific set or sets of ordered operations that control the functioning of the hardware and direct its operation, as known and understood by those skilled in the art. Note also, the dynamic noise filtering and signal restoration computer program 51, according to one or more of the embodiments of the present invention, need not reside in its entirety in volatile memory, but can be selectively loaded, as necessary, according to various methodologies as known and understood by those skilled in the art.

The system can also include a signal interfaces 53 connected through a cable 54 to a data acquisition unit (DAU) 55, which is connected to the computer 31. According to the exemplary configuration, the signal interface 53 comprises audio microphones or other form of acoustic signal capture or recording devices, such as accelerometers and geophones, capable of recording an acoustic (acoustic wave) signal. The data acquisition unit 55 receives the analog acoustic signal from the signal interface 53 and samples/digitize and stores the digitized acoustic signal in the database 43.

FIGS. 3A-17B provide graphics generated from a real example used to better illustrate exemplary embodiments of the invention. To provide exemplary graphs for discussion, an acoustic sound generated by a machine (not shown) was recorded by a measurement microphone and an accelerometer (not shown) for a period of over 71 hours to produce both an atypical microphone record and an atypical accelerometer record. Both the microphone and accelerometer have an internal built amplifier. They were fixed to a metal adaptor that was attached to the machine. The recorded acoustic signals were firstly amplified by the built in amplifier and then transmitted to DAU 55, where they were sampled and digitized. The signals from the two sensors were sampled at the same time sequence. The digitized data were transmitted to the computer 31 and saved in database 43 for analysis. The sampled data were in time domain format. They were each transformed into frequency domain format, i.e. amplitude spectrum format by applying Fast Fourier Transformation (FFT). Since both records from the two recording devices were sampled at the same time sequence, each piece of sound had two correspondent samples stored in the two correspondent records. For the benefit of clarity, letter A, for accelerometer, and M, for microphone, are added as suffix to the sample label. For example, Sample 1A and Sample 1M are the recoded pair samples of the same piece sound recorded by the accelerometer and the microphone respectively. For the benefit of convenience, letter "A" and "M" are added as suffix to any labels correspondent to the accelerometer and the microphone record respectively. Note, the example used in this disclosure is for the purpose of better explaining the principle only. In practice, one or more embodiments of the invention may be applied to other situations. Similarly, the various embodiments of the invention are not restricted to sensor types (i.e., microphone and accelerometer) used in this example, other types of acoustic sensor can also be employed.

Figure 3B:
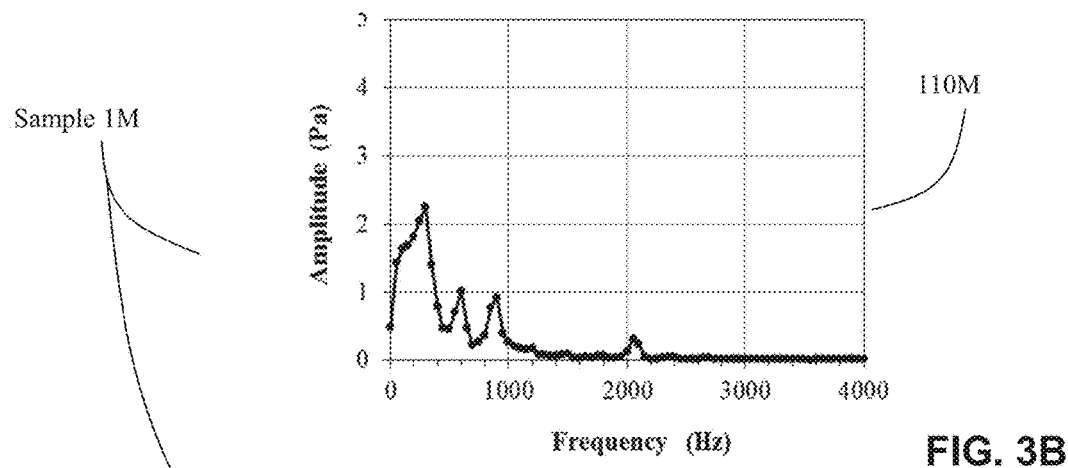
Figure 3C:
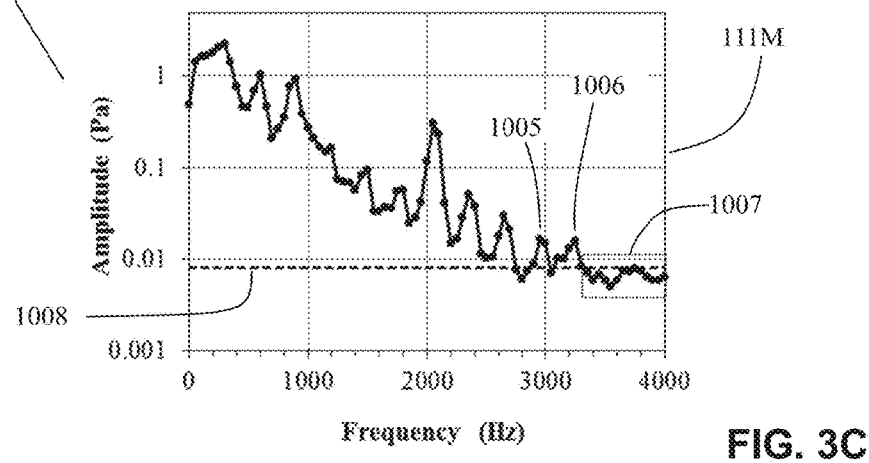

FIGS. 3A-3C is a set of graphs showing the amplitude spectrum of an acoustic signal sample recorded by the accelerometer (FIG. 3A) and the same acoustic signal (sound) sample recorded by the microphone (FIGS. 3B-3C). The sound sample recorded by the accelerometer is labeled "Sample 1A," and the sound sample recorded by the microphone is labeled "Sample 1M." A microphone produces an acoustic signal by measuring pressure change in air, and thus, the amplitude unit is Pascal (Pa); while an accelerometer records the acoustic signal by measuring acceleration of the vibration, and thus, the amplitude unit is Gravity Acceleration (g).

There exists background noise in the recorded sound. A portion of the background noise is shown framed at 1003 in the amplitude spectrum 110A of Sample 1A and is framed at 1007 the amplitude spectrum 111M of Sample 1M. The background noise is inherently generated by the audio signal recording system (e.g., microphone, cable, etc.) and from the surrounding environment. In fact, there is always background noise existing in recorded acoustic signals.

By comparing the amplitude spectrum 110A and 110M (see, e.g., FIG. 1A for overlay comparison), one can see that the spectrum patterns recorded by the accelerometer and microphone are the same for frequencies less than 1200 Hz. The frequency components of the amplitude spectrum 110M greater than 1200 Hz recorded by the microphone, however, significantly attenuate. The amplitude attenuation increases with the increase of frequency. As such, the quality of the acoustic signal 110M recorded by the microphone, is not only reduced by the background noise, but also significantly deteriorated by the attenuation of its high frequency components.

To increase the quality of acoustic signal, the signal should be filtered to remove the background noise, and the attenuated high frequency components should be restored as much as possible. The background noise should be removed first and then the attenuated high frequency components are restored by using the filtered or otherwise cleaned amplitude spectrum. If otherwise, the high frequency components are restored without the removal of the background noise, the background noise will generally be enlarged in the restored portion of the signal.

For illustration purpose, as shown in FIGS. 3A-3C, the sound samples from both the accelerometer and the microphone records are provided to represent raw noisy signals to be filtered to remove noise. The sound Sample 1M from the microphone record is used as an example of raw noisy and attenuated signal sample to be filtered and its high frequency components to be restored; and the sound Sample 1A from the accelerometer, whose high frequency components were not attenuated, is used as a reference to check the restoring result of the microphone sample 1M.

According to an exemplary embodiment, there are two major solution steps for filtering noise and restoring the attenuated high frequency components of acoustic signal samples. Firstly, samples of a record are filtered by using a "Dynamic Threshold." A "Dynamic Threshold" is a "Dynamic Amplitude Noise Cutoff" which is evaluated from a sample and is then applied to the same sample. Secondly, the attenuated high frequency components of the cleaned or filtered samples are restored.

Referring to the microphone Sample 1M in FIG. 3B, there appear to be no signals above 2200 Hz on the amplitude spectrum 110M. Referring to the accelerometer Sample 1A in FIG. 3A, however, the amplitude spectrum 110A shows there are four obvious peaks: peak 1001, peak 1002 and two peaks before the peak 1001. When the amplitude scale of 110M is changed to logarithmic scale 111M (see FIG. 3C), the correspondent four peaks are more clearly visualized on the amplitude spectrum 111M provided by the microphone. Among them peaks 1005 and 1006 correspond to the peaks 1001 and 1002 of amplitude spectrum 110A, respectively. By comparing the spectrum 110A and 111M, it is also clear that peaks of amplitude spectrum 111M match the ones of amplitude spectrum 110A near perfectly in terms of their frequencies, and that the amplitude of high frequency components of 110M attenuated significantly, and that the attenuation increased with the frequency. To avoid the noise being enlarged during restoration, the recorded raw data should be filtered to remove background noise. After filtering, the process continues on to restore the recoverable attenuated spectral components. After restoration, the microphone amplitude spectrum 110M should be similar to the accelerometer amplitude spectrum 110A.

Various embodiments of the invention are designed to address cases in which there are no prior clean signals or pattern of noise available. In such situations, the signal cannot be readily differentiated from noise by applying clean signal or noise patterns according to conventional signal conditioning systems.

According to the exemplary embodiment, all obvious peaks on an amplitude spectrum are treated as parts of the signal and the large featureless section on the amplitude spectrum is treated as background noise. For example, still referring to FIGS. 3A-3C, the peaks 1001 and 1002 of the spectrum 110A and peaks 1005 and 1006 of the spectrum 111M are treated as part of the signals; while the part encircled by the rectangles at 1003 of spectrum 110A and 1007 of spectrum 111M are treated as background noise.

Further, under each signal data point within the whole frequency range of the respective Sample 1A, 1M, there is background noise contribution to the amplitude. The amount of the contribution is treated the same, i.e., as the maximum level of amplitude of the spectrum located within the featureless part at 1003 on spectrum 110A, and 1007 on spectrum 111M.

To remove the background noise, a proper noise cutoff, such as 1004 on amplitude spectrum 110A (FIG. 3A) and 1008 on amplitude spectrum 111M (FIG. 3C), is required to separate signal from the background noise. Once a proper noise cutoff is obtained, the background noise can then be filtered by subtracting the amplitude cutoff from the raw amplitude spectrum, as specified by Equation (1):

$$A_{fi} = A_{ri} - N_c, \text{ if } A_{ri} > N_c$$

$$A_{fi} = 0, \text{ if } A_{ri} \leq N_c \quad (1)$$

wherein $A_{fi}$ is the amplitude of a data point, i, of a amplitude spectrum of a sample after filtering;

wherein $A_{ri}$ is the amplitude of the data point, i, on a raw amplitude spectrum before filtering; and wherein $N_c$ is the noise amplitude cutoff.

When filtering raw data, Equation (1) is applied to the whole interested frequency range of the sample. For example, for the sample 1M recorded data by the microphone, the spectral components are attenuated at least approximately to the same level as the background noise beyond 4000 Hz. The interested frequency range is therefore 0-4000 Hz. From this discussion, it should be understood by one of ordinary skill that a proper noise cutoff is important in applying the above scheme, and that a proper noise cutoff should both maximally remove noise and also maximally preserve signals.

Figure 4A:
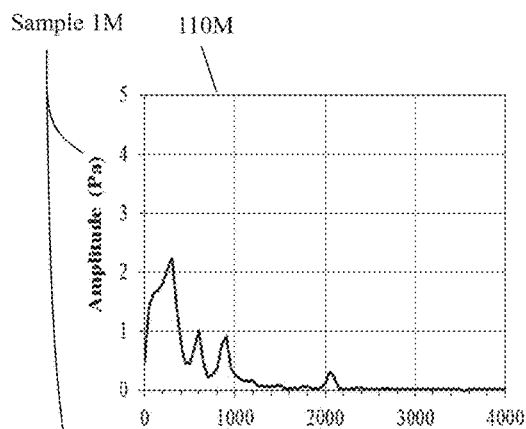
FIGS. 4A-4D are a set of graphs showing amplitude spectrums of two samples to illustrate that the level of the background noise is time-varying.
Figure 4C:
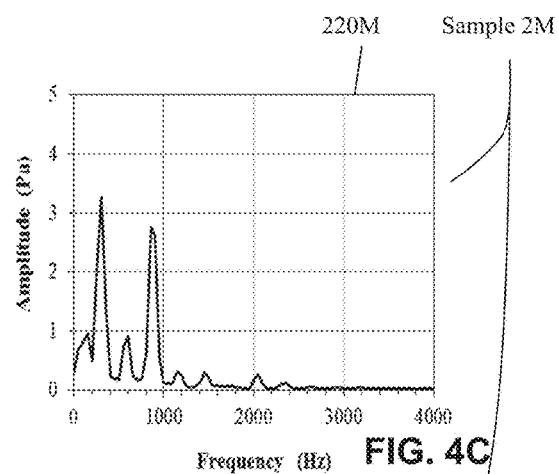
Figure 4B:
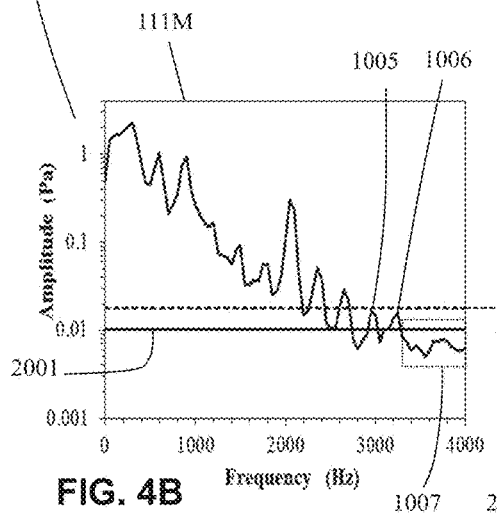
Figure 4D:
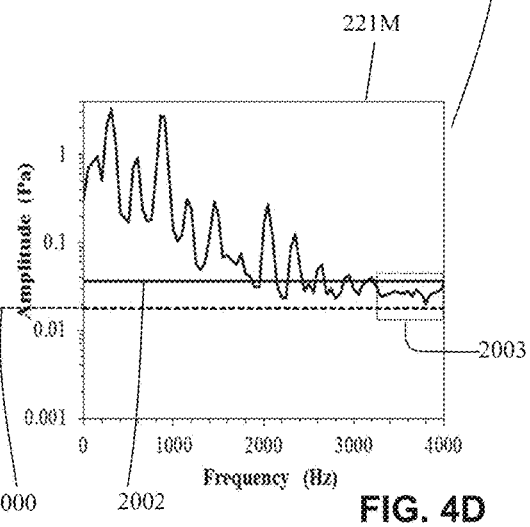

FIGS. 4A-4D provide amplitude spectrum diagrams of two samples, Sample 1M and 2M, recorded at different times to illustrate that the level of the background noise is time-varying. Amplitude spectrum 111M in FIG. 4B is the same as amplitude spectrum 110M in FIG. 4A, but with the amplitude axis in logarithmic scale. The Sample 1M in this diagram is the same sample as in FIGS. 3B-3C. Amplitude spectrum 221M in FIG. 4D is also the same as amplitude spectrum 220M in FIG. 4C, but with the amplitude axis in logarithmic scale. This set of figures, however, comparatively illustrates that background noise is not constant, but rather, can be time-varying. The level of background noise 1007 (FIG. 4B) of the sample 1M is significantly different from that of the background noise 2003 (FIG. 4D) of the sample 2M.

It can be seen from this comparative illustration that applying a constant noise cutoff to these two samples would lead to erroneous results. For example, if a constant noise cutoff 2000 (extending across FIGS. 4B and 4D) is applied, the two signal peaks, 1005 and 1006 of the amplitude spectrum 111M of the sample 1M will be removed since their amplitudes are less than the constant cutoff 2000, and the background noise 2003 of the spectrum 221M of the sample 2M will not be removed because the amplitudes of the background noise 2003 are above the constant cutoff 2000.

This illustration demonstrates that applying a constant amplitude noise cutoff in the filtering could remove some components of signal and omit some background noise. In the ideal case, a specific noise cutoff should be selected for a specific sample, such as the cutoff 2001 for sample 1M (FIG. 4B) and the cutoff 2002 for sample 2M (FIG. 4D), to best separate signal from the background noise. In summary, constant noise cutoff should not be applied to the situations in which the noise is time-varying. As such, according to the exemplary configuration, a more optimal approach is provided that evaluates a cutoff for a specific sample and applies the cutoff to the same sample.

Figure 5A:
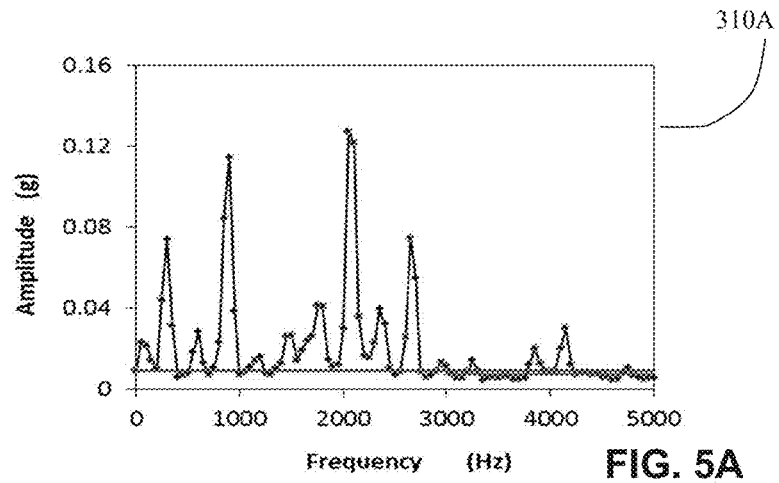
FIGS. 5A-5C are a set of graphs showing amplitude spectrums of a sample to illustrate proper selection of a Dynamic Amplitude Noise Cutoff for use in noise filtering according to an embodiment of the invention.
Figure 5B:
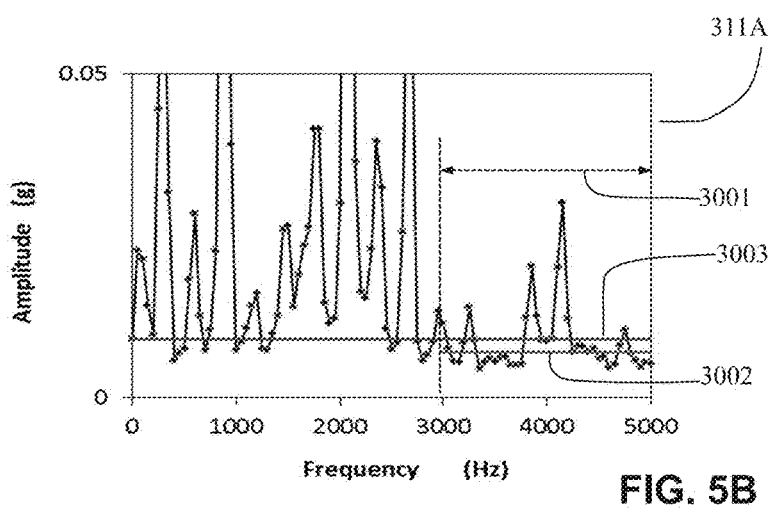
Figure 5C:
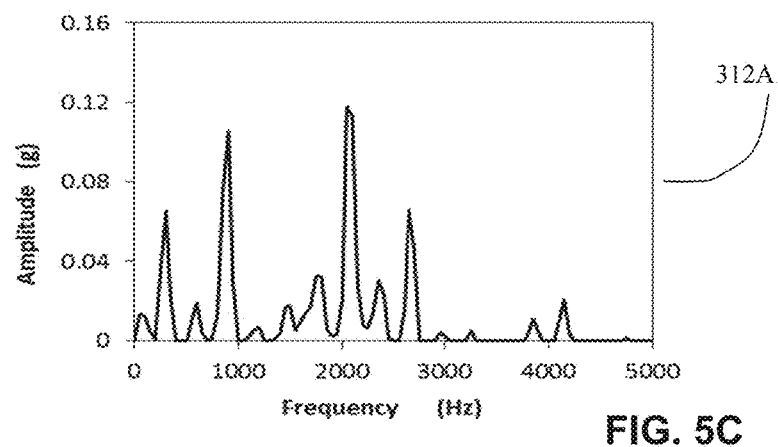

A good noise cutoff is the one derived from a sample and is applied to the same sample. An exemplary embodiment of the invention provides such methodology. Referring to FIGS. 5A-5C, sample 3A, recorded by the accelerometer, provides an example to explain the principle. The spectrum diagram 311A (FIG. 5B) shows the zoomed in amplitude of the spectrum 310A (FIG. 5A). Spectrum 312A (FIG. 5C) is the filtered result of the spectrum 310A after applying the methodology disclosed in this aspect of the invention. In the spectrums 310A and 311A, each dot is a data point.

As shown in FIG. 5B, within a frequency range, for example 3000-5000 Hz (at 3001) of the amplitude spectrum diagram 311A, we can be certain that, for a given record, there exists a $K^{th}$ percentile below which the data points, or components of all samples within the record can be certainly treated as background noise. For example, $50^{th}$ percentile, at 3002 of the spectrum 311A, is such an amplitude percentile. This percentile is named herein as the "Base Noise Percentile."

The definition of Base Noise Percentile will not, however, ensure that all data points above it are signals. For example, 50th percentile, at 3002, of the frequency range 3000-5000 Hz of the diagram 311A in FIG. 5B is a Base Noise Percentile for the record. For the sample 3A, the data points between the Base Noise Percentile 3002 and the line 3003 of the amplitude spectrum 311A are also background noise, although they are above the Base Noise Percentile 3002.

For a given record, there exists not only one Base Noise Percentile according to its definition. When a Base Noise Percentile is determined for a record, any percentile below the determined Based Noise Percentile is a Base Noise Percentile. For example, since the 50th percentile 3002 of the diagram 311A of the FIG. 5B is a Base Noise Percentile, the 40th percentile is also a Base Noise Percentile, simply because all the data points below it will be lower than the 50th percentile.

The Base Noise Percentile cannot be used directly as the noise cutoff for a given record because there are very possibly some noise data points above it that cannot be removed after filtering the record. Since below a Base Noise Percentile, all data points are treated as noise and there are still noise data points above the Base Noise Percentile, a proper amplitude noise cutoff must be above the Base Noise Percentile.

An exemplary embodiment of the invention provides such a proper amplitude cutoff, termed as "Dynamic Threshold", or "Dynamic Amplitude Noise Cutoff." This amplitude noise cutoff is dynamic since it is evaluated for each individual sample within a record and is applied to the same individual sample. As a result, it is capable to optimally separate noise from signals; that is, to remove noise maximally and to preserve signals maximally during filtering.

Since for a given record, the Dynamic Amplitude Noise Cutoff is above a Base Noise Percentile, the following equation Equation (2) has been constructed to define such threshold cutoff:

$$A_{th} = C_{th} \cdot P_b \quad (2)$$

wherein $A_{th}$ is the Dynamic Amplitude Noise Cutoff, the unit being the same as the amplitude of the amplitude spectrum. The line 3003 on amplitude spectrum 311A of the FIG. 5B is such a cutoff.

wherein $P_b$ is a Base Noise Percentile for a given record, the unit being the same as the amplitude of the amplitude spectrum. The line 3002 on amplitude spectrum 311A of the FIG. 5B is a Base Noise Percentile for the sample 3A. The definition of percentile and the evaluation of a percentile will be readily understood by those skilled in the art.

wherein $C_{th}$ is a constant coefficient, named as Threshold Factor. It is a unitless constant for a given record.

The frequency range within which the Base Noise Percentile is derived, is termed the "Specific Frequency Range." For a given record, the Specific Frequency Range is the same for all samples within the record. For example, the frequency range 3000-4000 Hz is chosen as the Specific Frequency Range for the microphone record, and the frequency range 3000-5000 Hz is chosen as the Specific Frequency Range for the accelerometer record in this example.

The Base Noise Percentile $P_b$ is also the same for all samples within a given record in this embodiment of the invention. For example, the 50th percentile is chosen as the Base Noise Percentile for both the microphone record and the accelerometer record of this example. The 50th percentile was chosen for both records because it provides an adequate reference percentile for both records. A different percentile, however, can be used as the Base Noise Percentile for the two records. Note, although the Base Noise Percentile is the same for all samples in a given record, the actual amplitude value for each sample that the percentile equates to is evaluated from the sample, and thus, will normally be different from that of each other sample in the record.

The Threshold Factor, $C_{th}$, is constant for a given record, and thus, is the same for all samples within the given record.

Rooted in its definition in the Equation (2), the Dynamic Amplitude Noise Cutoff, $A_{th}$, has following property: it uses the noise information of a whole record, namely the Threshold Factor, $C_{th}$, the same "Specific Frequency Range" for the whole record, and the same Base Noise Percentile for the whole record, and it is tailored to each sample by using the specific amplitude value of the Base Noise Percentile, $P_b$, of the sample, at the respective Base Noise Percentile.

When the background noise varies, the value of the Base Noise Percentile follows the background noise variation. The Threshold Factor, $C_{th}$, makes the Dynamic Amplitude Noise Cutoff above the background noise and below the signals.

As a result, Dynamic Amplitude Noise Cutoff follows the background noise variation and at least substantially, if not completely, maximally separates background noise from the signals.

It was found out that following alternative definition of the Dynamic Amplitude Noise Cutoff has the similar effectiveness as the one defined in Equation (2) for separating background noise from signals:

$$A_{th} = P_b + C_e \quad (3)$$

wherein, $C_e$ is a constant coefficient, named as Threshold Elevator, the unit being the same as the amplitude of the amplitude spectrum. It is constant for a given record. Its function, the same as that of the Threshold Factor, $C_{th}$, is to make the Dynamic Amplitude Noise Cutoff above the background noise and below the signals, and thus, at least substantially, if not completely maximally separate the background noise from the signals.

Using the Dynamic Amplitude Noise Cutoff, the background noise can be maximally removed and the signals can be maximally preserved by using the Equation (1). When using the Equation (1) the noise cutoff, $N_e$ is replaced by the Dynamic Amplitude Noise Cutoff, $A_{th}$, to form Equation (4):

$$A_{f_i} = A_{r_i} - A_{th}, \text{ if } A_{r_i} > N_{th}$$

$$A_{f_i} = 0, \text{ if } A_{r_i} \leq A_{th} \quad (4)$$

Figure 6:
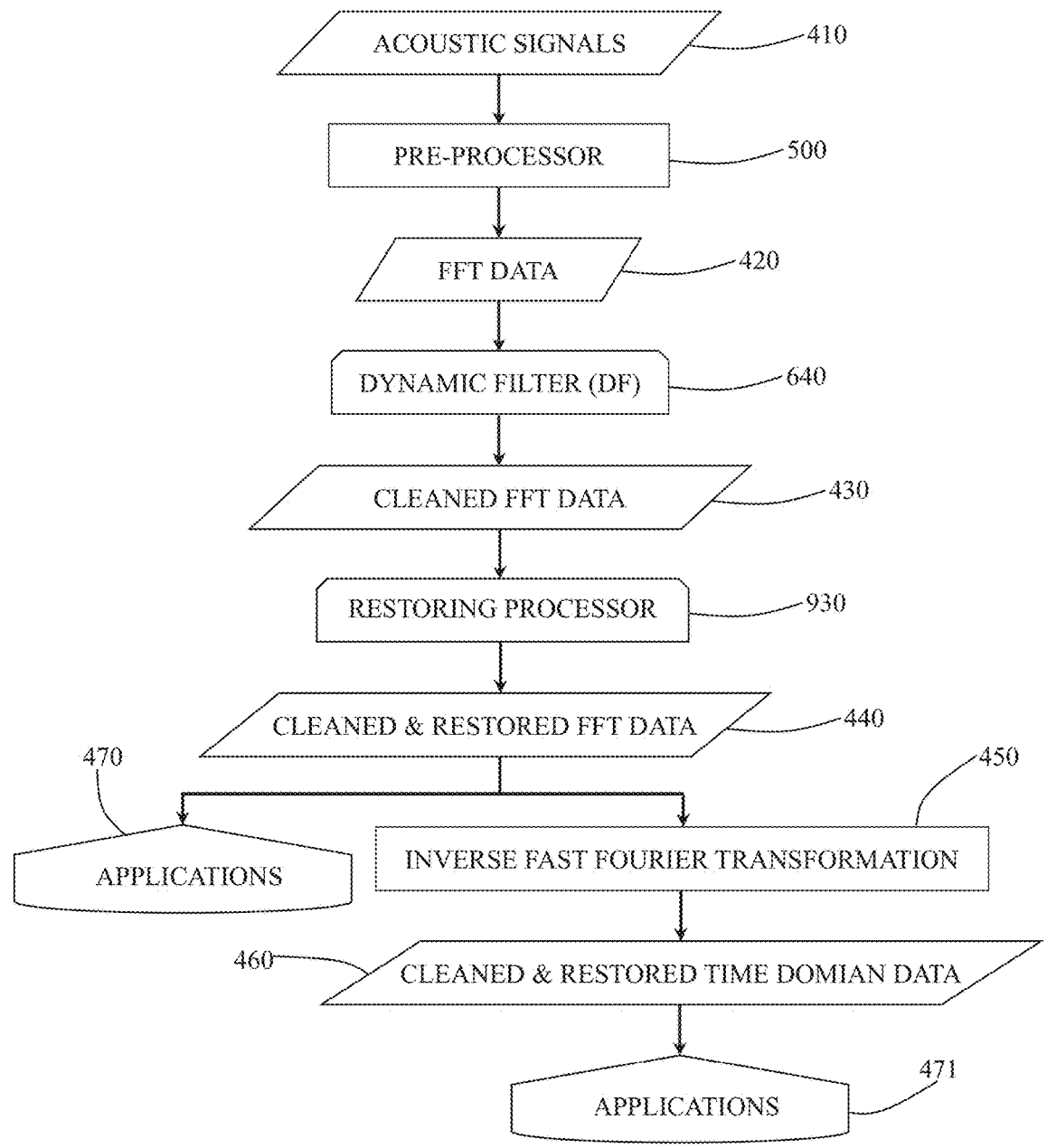
FIG. 6 is a schematic high level flow diagram illustrating steps for filtering background noise and restoring attenuated high frequency components of acoustic signals using a "Dynamic Amplitude Noise Cutoff" filtering technique according to an embodiment of the present invention.

Procedure for Filtering and Restoring a Record. FIG. 6 is a high level flow diagram illustrating steps for filtering background noise and restoring attenuated high frequency components of acoustic signals using the "Dynamic Amplitude Noise Cutoff" filtering technique, according to an exemplary embodiment.

When raw acoustic signals 410 are received, they are transformed into frequency domain data (FFT data 420) by a Pre-processor 500. The FFT data, when plotted, are called amplitude spectrum. Amplitude spectrums 110M in FIG. 4A, 220M in FIG. 4C and 310A in FIG. 5A, provide examples of plotted FFT data.

The FFT data is passed through Dynamic Filter 640 to filter background noise, and thus, produce Cleaned FFT Data 430.

The Cleaned FFT Data 430 is treated by a Restoring Processor 930 to restore the attenuated high frequency components of the record, and thus, produce Cleaned & Restored FFT Data 440.

The Cleaned & Restored FFT data 440 can be used directly in user's Applications 470. The Cleaned & Restored FFT Data 440, which is in the frequency domain format, can also be inversed by applying an Inverse Fast Fourier Transformation 450 to convert the Cleaned & Restored FFT data 440 into Cleaned & Restored Time Domain Data 460, which can be used directly in user's applications 471, such as being played back by an acoustic device.

The above described filtering and restoration procedure can be applied to acoustic data for both recorded records and online records of real-time acoustic signals as understood by those of ordinary skilled in the art.

Figure 7:
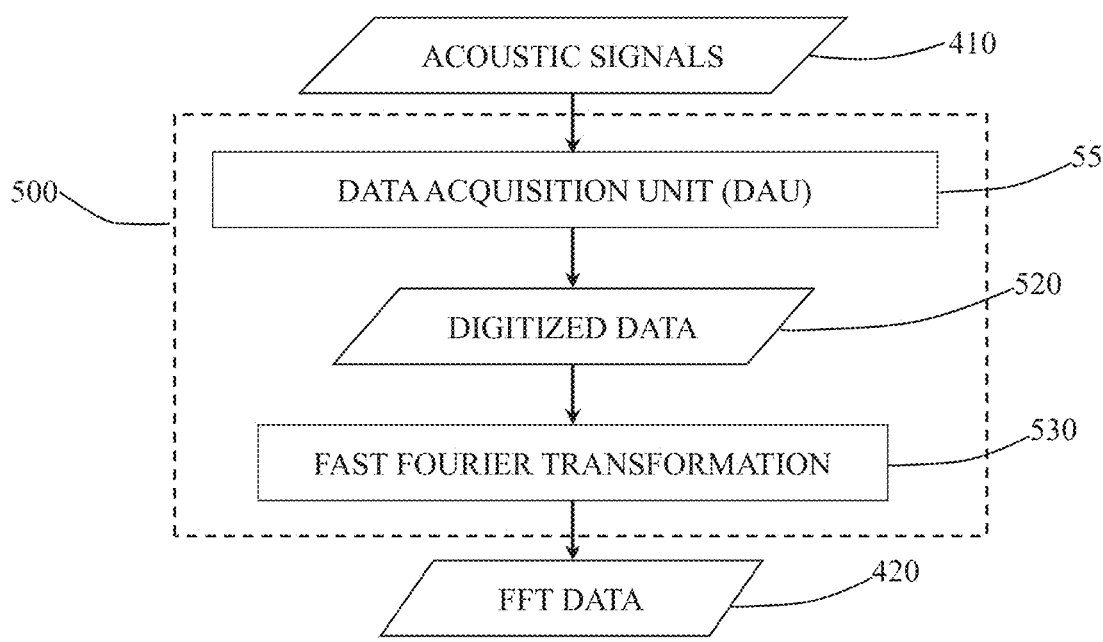
FIG. 7 is a schematic flow diagram illustrating steps for forming Fast Fourier Transform data for application to a Dynamic Filter according to an embodiment of the invention.

As shown in FIG. 7, according to an exemplary configuration, the Pre-processor 500 in FIG. 6, employed to produce FFT data from acoustic signals, includes two major steps. First, Acoustic Signals 410, which are in analog format, are sampled and digitized by using a Data Acquisition Unit (DAU) 55 into Digitized Data 520 according to this exemplary embodiment. Second, the Digitized Data 520, which is in time domain format, is transformed by Fast Fourier Transformation 530 into FFT Data 420, which is in frequency domain. The above procedure for producing FFT data from acoustic signals is well understood by those skilled in the art. A Data Acquisition Unit is also known to those skilled in the art as an Analog-to-Digit Converter.

The center of the Dynamic Filter 640 (FIG. 6) is the Equations (2), (3) and (4). By applying the Equations (2) and (4) or (3) and (4) to each sample one-by-one in a record, the background noise of the record is removed from the entire record.

For a given record, before FFT Data 420 is filtered by Dynamic Filter 640, the Dynamic Filter should be tuned in order to optimally separate the background noise from the signals.

To "tune" the Dynamic Filter is to determine a proper percentile as the Base Noise Percentile $P_b$, and to adjust the Threshold Factor, $C_{th}$, or Threshold Elevator $C_e$ for the Equation (2) or (3). Since only one of the equations (2) and (3) is used in filtering, and the procedure for adjusting the Threshold Factor, $C_{th}$, and Threshold Elevator $C_e$ is the same. As such, for brevity, only one parameter, the Threshold Factor, $C_{th}$ was chosen to illustrate the tuning procedure.

Figure 8:
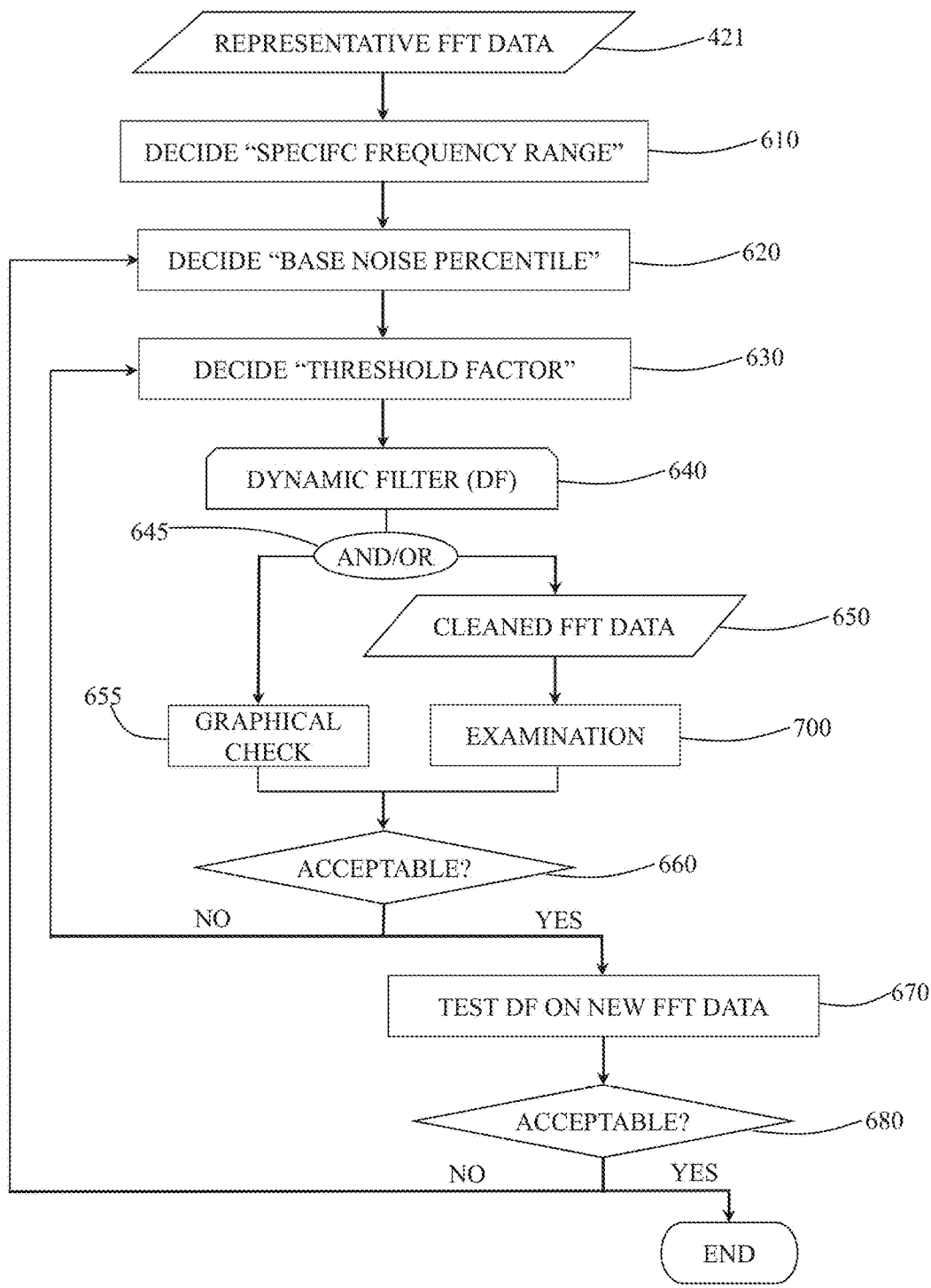
FIG. 8 is a schematic high-level flow diagram illustrating a process for tuning the Dynamic Filter according to an embodiment of the invention.

FIG. 8 provides a high-level flow diagram describing an exemplary process for tuning the Dynamic Filter 640. At the beginning of the process, Representative FFT Data 421 is used in tuning the Dynamic Filter. There are two primary scenarios in selecting the Representative FFT Data 421. First, if the record is a recorded one, FFT data recorded at different times with different background noise levels are used as the Representative FFT Data 421. Second, if an online record is to be processed and its FFT data can't be selected at different times, some FFT data recorded at the beginning of the record are used as the Representative FFT Data 421. In both scenarios, the Representative FFT Data is selected from the record which is going to be/being processed.

The next step 610 is to determine the "Specific Frequency Range." As described previously, the Specific Frequency Range is a frequency range within which a Base Noise Percentile can be readily determined for all samples with the given record. For example, within the frequency range 3000-5000 Hz, (at 3001) of the amplitude spectrum 311A of the FIG. 5B, it can be certain that, below 50$^{th}$ Percentile (at 3002), all data points are background noise.

As demonstrated by the example of FIG. 5B, for a given record, it will be easier to decide a Base Noise Percentile within a frequency range which is dominated by background noise. Therefore, if a frequency range dominated by background noise exists for a given record, it should be chosen as the Specific Frequency Range. Otherwise, a frequency range with the highest portion of background noise data points is chosen as the Specific Frequency Range. A Specific Frequency Range should be wide enough, to ensure that the value of Base Noise Percentile is stable.

Correspondingly, the samples of the Representative FFT Data 421 are checked to find a wide frequency range which is dominated by background noise as the Specific Frequency Range. If such a frequency range does not exit, then a wide frequency range with highest portion of background noise data points is chosen as the Specific Frequency Range.

At step 620, a "Base Noise Percentile" is decided. As defined previously, a "Base Noise Percentile" is a percentile below which the data points within the Specific Frequency Range on the amplitude spectrum can, with certainty, be treated as noise for all the samples within the record. To optimally separate background noise from signals, a "Base Noise Percentile" should be high. Choosing a too high "Base Noise Percentile," however, would increase the probability of signals with low amplitudes being treated as background noise. That is, a too high value would result in over filtering.

As introduced earlier, the Threshold Factor, $C_{th}$ is used to increase a Base Noise Percentile to a Noise Cutoff of a higher level (see, e.g., FIG. 5B). Accordingly, it has been found to be disadvantageous to risk choosing an excessively high Base Noise Percentile. It is, however, also disadvantageous to choose an excessively low Base Noise Percentile because it will increase the probability of under filtering.

In summary, at step 620, deciding "Base Noise Percentile" involves choosing an apparent dividing line under which all the data points within the decided "Specific Frequency Range" can be readily considered to be background noise for all the samples within the Representative FFT Data 421. For example, the 50$^{th}$ percentile 3002 on FIG. 5B can be readily and apparently considered to be a good candidate for the "Base Noise Percentile".

When a "Base Noise Percentile", say 50%, is chosen, the value of the "Base Noise Percentile" within the decided "Specific Frequency Range" is evaluated for each sample within the Representative FFT Data 421. The method for evaluation of the value of a percentile is well understood and well known to those skilled in the art. Then, for each sample within the Representative FFT Data 421, the data points within the decided "Specific Frequency Range" are compared against the evaluated value of the "Base Noise Percentile" for the sample to see if all the data points below the value of the "Base Noise Percentile" are treated noise data, and if most of the noise data points are below the value of the "Base Noise Percentile". If it is, then the chosen "Base Noise Percentile" is accepted as the right one.

If for some samples, some data points below the value of the "Base Noise Percentile" are not treated noise data, but signal data, the "Base Noise Percentile" is too high; it should be decreased, for example, from 50% to 45%. Or if, for some samples, the majority of the considered background noise data are not below the value of the "Base Noise Percentile", the "Base Noise Percentile" is too low and should be increased. Note, it is allowable if some noise data points are above the value of the "Base Noise Percentile" when deciding a proper "Base Noise Percentile", since signal data points will be separated from the noise data points by the "Dynamic Amplitude Noise Cutoff", which is higher than the value of the "Base Noise Percentile".

At step 630, the Threshold Factor $C_{th}$ is decided. If the Equation (3) is used, then the Threshold Elevator $C_e$ is decided or otherwise identified. Because the procedure for identifying the two parameters are the same, only one parameter, the Threshold Factor, $C_{th}$ is chosen to illustrate the procedure.

An initial value for the Threshold Factor $C_{th}$ is chosen. Responsibly, the corresponding Dynamic Amplitude Noise Cutoff can be evaluated for a given sample from its Base Noise Percentile and the initial Threshold Factor. This given sample can be filtered by using the Equation (4).

The performance of this initial Dynamic Filter 640, defined by the combination of Equations (2) and (4) or Equations (3) and (4), is then examined. The initial Dynamic Filter 640 can be checked or otherwise examined directly, at the step 655, by testing the Dynamic Filter 640 with each sample within the Representative FFT Data 421 using a graphic such as, for example, the acoustic spectrum 311A graphic of FIG. 5B, to visually examine whether or not the Dynamic Amplitude Noise Cutoff 3003 is positioned to optimally separate background noise from the signals.

Also or alternatively, the initial Dynamic Filter 640 can be examined by filtering each sample within the Representative FFT Data 421 using the initial Dynamic Filter 640 to produce Cleaned FFT Data 650. The cleaned FFT Data 650 is then examined at step 700.

Figure 9:
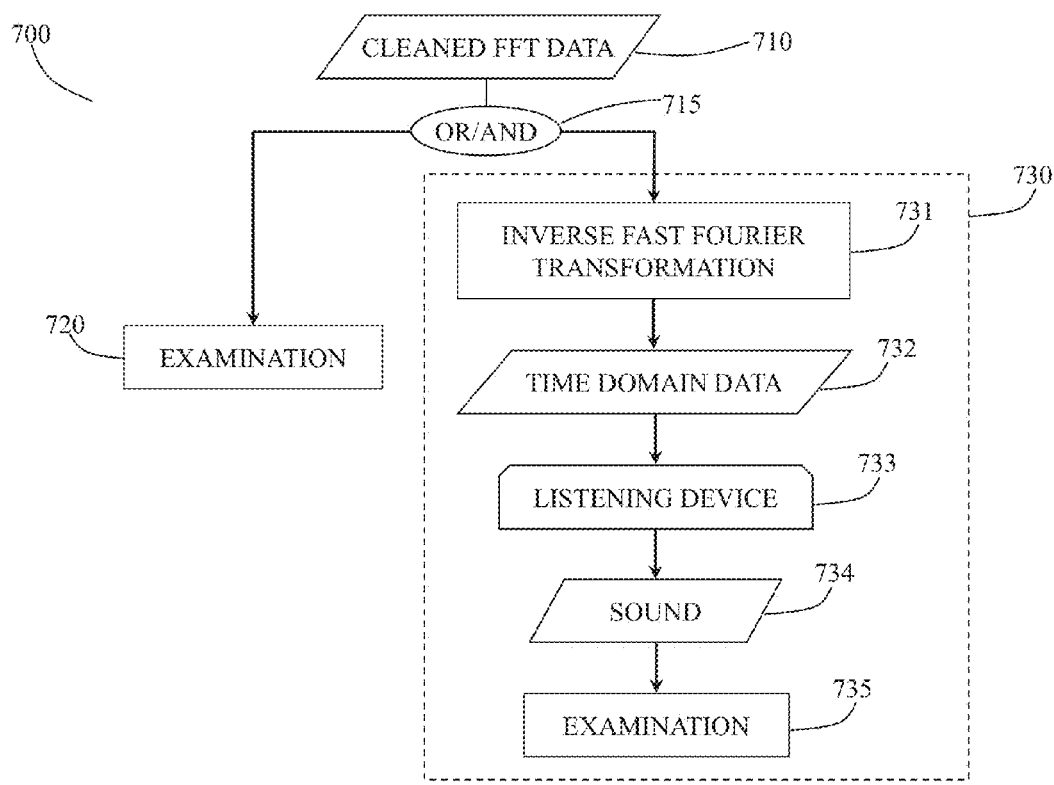
FIG. 9 is a schematic flow diagram illustrating examination of cleaned FFT data, or cleaned and restored FFT data according to an embodiment of the invention.

FIG. 9 provides a high-level flow diagram describing the examination step 700 according to an exemplary embodiment. The Cleaned FFT Data 710 in the FIG. 9 is the Cleaned FFT Data 650 in FIG. 8. The Cleaned FFT Data 650 is either directly examined at the step 720 by comparing each of its samples against the respective one of the raw Representative FFT Data 421, and/or is transformed into Time Domain Data 732 by Inverse Fast Fourier Transformation 731. The Time Domain Data 732 can be played back by a Listening Device 733, and the Sound 734 is then examined at step 735.

Referring again to FIG. 8, after an Examination 700 and/or graphical check 655, a judgment is made at step 660 to conclude if the initial Dynamic Filter is acceptable. If it is not acceptable at step 660, then the Dynamic Filter needs further tuning by adjusting the value of the Threshold Factor back at the step 630. Then the steps are repeated up to the step 660.

If it is acceptable at the step 660, the initial Dynamic Filter is tested at step 670 with a new small set of Representative FFT data. The procedure of "Test DF on New FFT Data" 670 is identical to that of the examination with the Representative FFT Data 421. It is accomplished by following the steps from 645 to 660, but on the new set of Representative FFT data.

If the test is not acceptable at the step 680, then we need to tune the Dynamic Filter 640 further by repeating the procedure from the step 620. If it is acceptable at the step 680, then the Dynamic Filter 640 is tuned and can be readily applied to filter the record.

For the example test being described herein, there are over 51,400 samples in the exemplary microphone record and in the exemplary accelerometer record. Of the 51,400 samples, thirty samples recorded at different time were selected as the Represented FFT Data. From the Representative FFT Data, it was determined that 3000-4000 Hz was a proper Specific Frequency Range for the microphone record as indicated, for example, by the two samples in FIGS. 4A-4D, and 3000-5000 Hz for the accelerometer record indicated, for example, by the sample 3A in FIGS. 5A-5C. It can be readily observed from the respective figures that for all 30 samples, all the data points within the Specific Frequency Range below $50^{th}$ percentile are background noise for both the microphone and accelerometer data. Therefore, the $50^{th}$ percentile was decided as the Base Noise Percentile for both the microphone and accelerometer records. By following the steps from 630 onwards in FIG. 8, it was found that 1.4 and 1.3 is the best value of the Threshold Factor, $C_{th}$ for the microphone and accelerometer records, respectively. Now the Equation (2) is fixed for the example records, i.e. the Dynamic Filter is tuned for each of the example records.

Lines 2001 and 2002 in FIGS. 4B and 4D, respectively, mark the Dynamic Amplitude Noise Cutoff calculated using the fixed Equation (2) for the sample 1M and 2M respectively; and line 3003 in FIG. 5B mark the Dynamic Amplitude Noise Cutoff for the sample 3A.

Figure 10A:
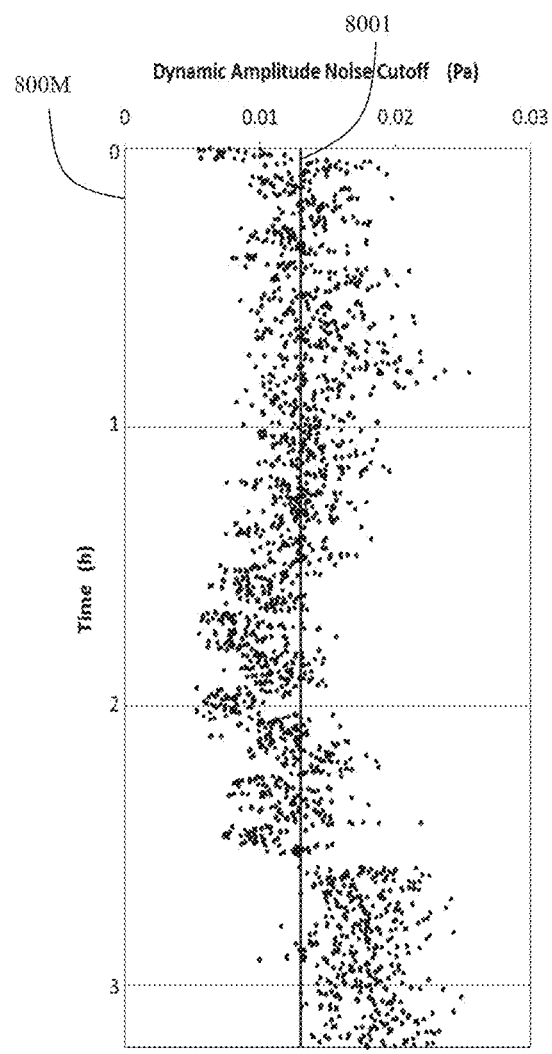
FIGS. 10A-10B is a pair of graphs showing derived Dynamic Amplitude Noise Cutoff values for microphone and accelerometer records, respectively, according to an embodiment of the invention, in comparison to a constant noise cutoff line.
Figure 10B:
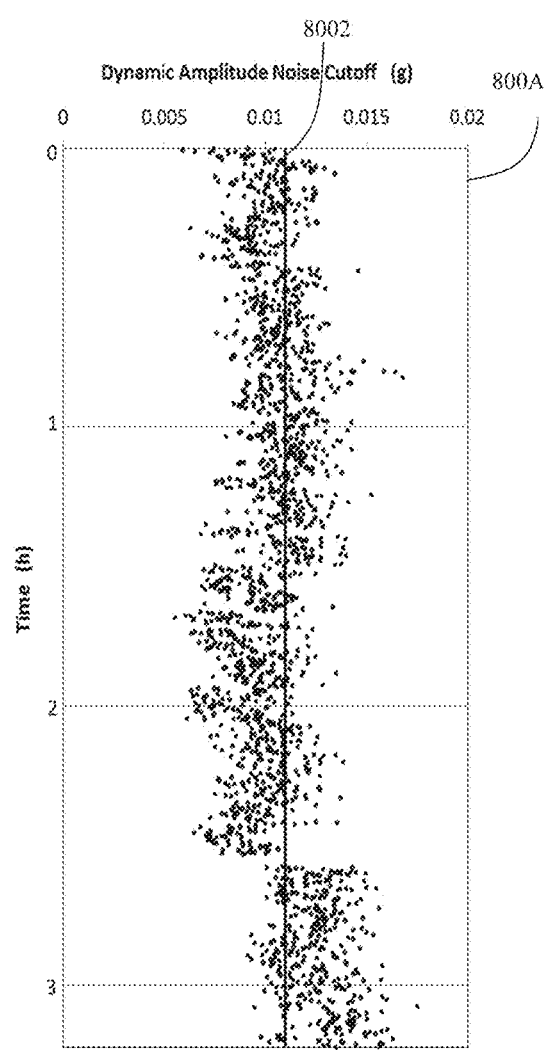

FIGS. 10A-10B show the derived Dynamic Amplitude Noise Cutoff using the tuned Equation (2) for part of the exemplary microphone and accelerometer records, 800M for the microphone and 800A accelerometer, respectively. The figures also show that the Dynamic Amplitude Noise Cutoff varies with time. If a constant noise cutoff, such as the vertical line 8001 for the microphone record, and the vertical line 8002 for the accelerometer record is used, any sample on the left of the constant cutoff will be over filtered, i.e., signals are either removed or suppressed; and any sample on the right of the constant cutoff will be under filtered, i.e., noise will not be maximally or otherwise optimally filtered.

As such, these exemplary plots show that employment of a constant amplitude cutoff generally results in poor quality filtering. As such, a fixed value should not be used as a noise cutoff. If it is used, it would be the equivalent of an assumption that the amplitude of the background noise is the same for all samples within a given record. This assumption, however, although often made, is not a valid assumption.

Additionally, a percentile, e.g., the $50^{th}$ percentile, alone, should also not be used as a noise cutoff to separate noise from data. If it is used, it would be the equivalent of an assumption that within the Specific Frequency Range the proportion of noise data points is the same for all samples within a given record. That is, it would be the equivalent of an assumption that all of the samples within a given record have the same percentage of error data points. This assumption is also not a valid assumption.

According to the exemplary embodiment, one can safely and easily find a percentile "Base noise percentile" below which all the data points are noise. Then the best separator between noise and signal data points is above the "Base Noise Percentile". An adjusted (tuned) "Threshold Factor" will then make the "Dynamic Amplitude Noise Cutoff" the best separator between noise and signal data points. Since for each sample within a given record, the value of "Base Noise Percentile" is evaluated from the data of the sample, i.e. evaluated for the sample, and applied to the same sample through the "Dynamic Amplitude Noise Cutoff", this embodiment and others optimally separates background noise from signals.

As described previously, during transmitting and recording, the high frequency components of acoustic signals may attenuate more than the lower frequency components. That is, attenuation is a function of frequency. The flow diagram of FIG. 11 includes a Restoring Processor 930 used to restore attenuated signals. The Restoring Processor 930 comprises the following two Equations:

$$A_{fr\_i} = G_i \cdot A_{f\_i} \tag{5}$$

$$G_i = f(F_i), \; G_i \geq 1 \tag{6}$$

wherein $A_{fr\_i}$ is the amplitude of the data point i after filtering and restoring;

wherein $A_{f\_i}$ is the amplitude of the data point, i, of a sample, after filtering;

wherein $G_{\_i}$, unitless, is Gain applied to the data point i; and wherein $F_{\_i}$ is the frequency at the data point i.

Equation (6) is a generic form for the relationship between Gain and frequency, termed the "Gain Function." To restore the attenuated amplitude, the attenuated amplitude is amplified by using the Equation (5) to maximally restore the attenuated amplitude using proper Gain. Since the attenuation is frequency dependent, as indicated by Equation (6), the Gain is frequency dependent. Because attenuation depends on many factors, such as the media in which the acoustic wave transmits, the recording environment, and the recording device, among others, there would be different suitable forms of the Equation (6) for different scenarios. Therefore, a generic, not a specific form of the Equation (6) is presented in this example. In operation, however, a suitable specific form should be determined or selected for the specific situation, such as, for example, the example shown in FIG. 12.

For a given record, the value of Dynamic Amplitude Noise Cutoff varies from sample to sample, but is constant for a given sample, i.e., in accordance with Equations (2) or (3), it does not vary with frequency for the given sample. The value of Gain, however, varies with frequency, but is independent of samples; i.e. for a part or whole record, the Gain function is constant. When the Gain Function, Equation (6), is considered to be fixed for a given record, the Restoring Processor 930 can be used to restore attenuated signals. That is, to restore a record, Equation (5) is applied to each sample one by one in sequence until all the samples in the record are restored.

Figure 11:
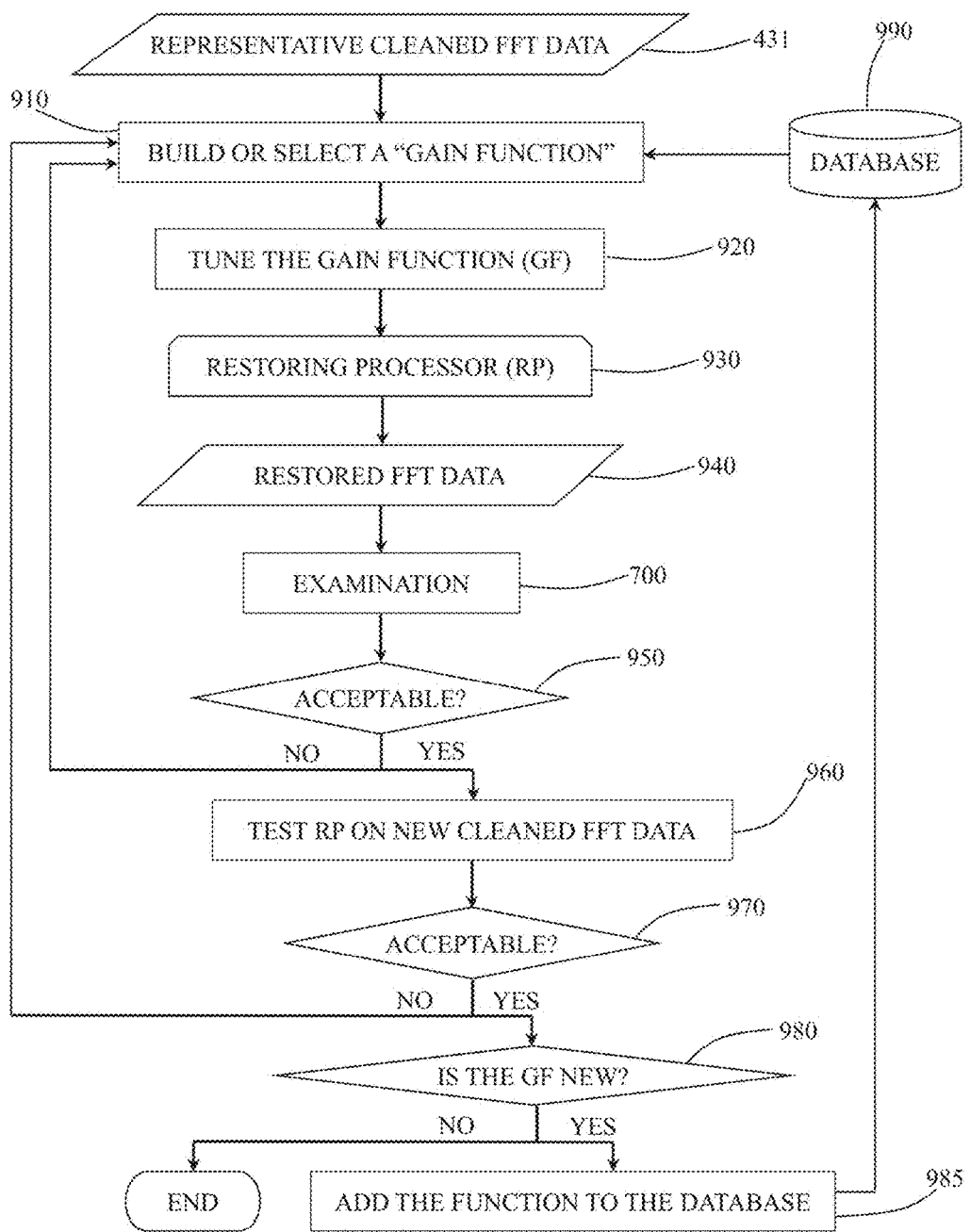
FIG. 11 is a schematic flow diagram illustrating steps for restoring attenuated high-frequency components of an acoustic audio signal and to determine or select and tune a Gain Function according to an embodiment of the invention.

For a given record, before the Restoring Processor 930 can be applied, the Gain Function (Equation (6)) is to be decided or selected and tuned optimally. FIG. 11 is a high-level flow diagram illustrating the step-by-step procedure to determine/identify or select, and then tune a Gain Function. Some Representative Cleaned FFT Data 431 is selected and used in tuning the procedure. There are two scenarios in selecting Representative Cleaned FFT Data 431. First, if the record is a recorded one, Cleaned FFT data recorded at different times with different background noise levels are used as the Representative Cleaned FFT Data 431. Second, if an online record is being processed substantially in real time, and thus, its FFT data cannot be readily selected at substantially different times, some cleaned FFT data recorded at the beginning of the record are used as the Representative Cleaned FFT Data 431. Note, it should be understood that Representative Cleaned FFT Data is selected from the same record to be processed regardless of whether or not the record was previously stored or presently being received and processed.

Figure 12:
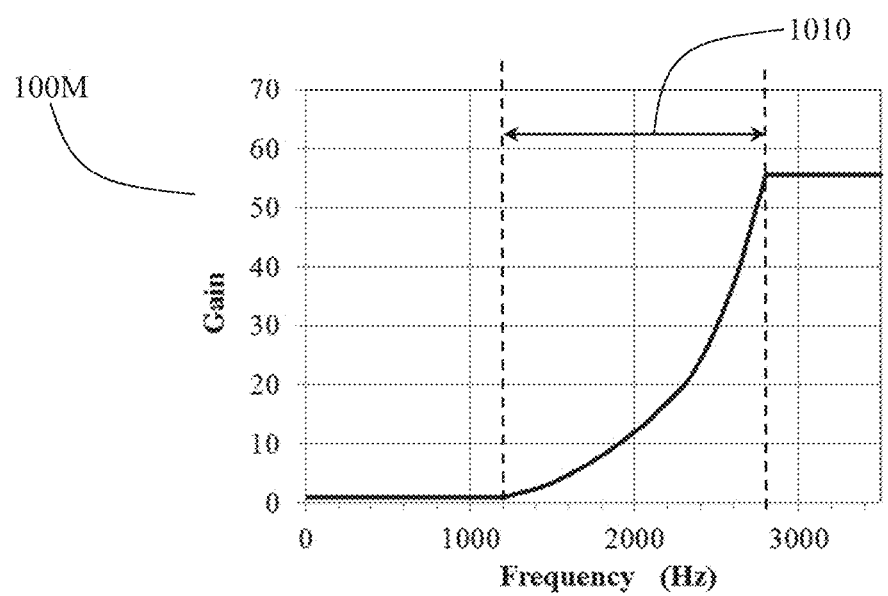
FIG. 12 is a graph showing an exemplary Gain Function used in restoring attenuated high-frequency components of an acoustic signal according to an embodiment of the invention.
Figure 13A:
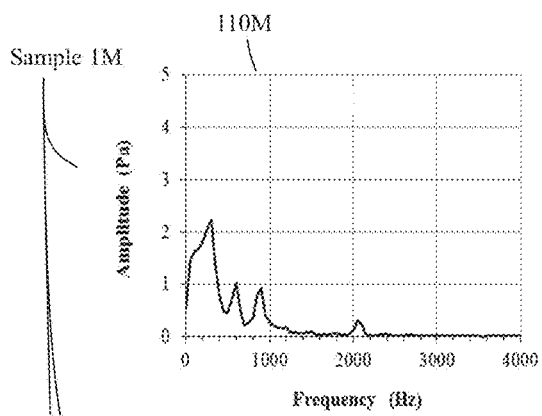
FIGS. 13A-13E are a set of graphs showing raw microphone and accelerometer FFT sample data and filtered and/or restored results for a pair of samples recorded by a microphone and an accelerometer, respectively, during an identical time frame of the sound, according to an embodiment of the invention.
Figure 13B:
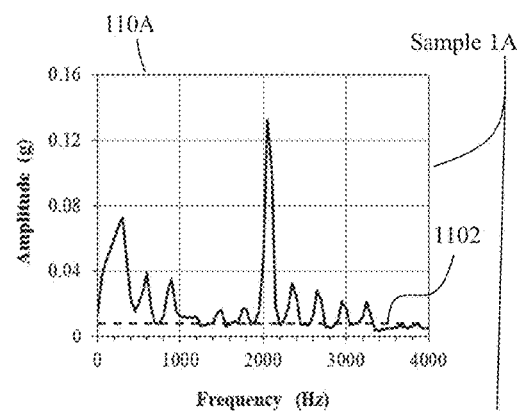
Figure 13C:
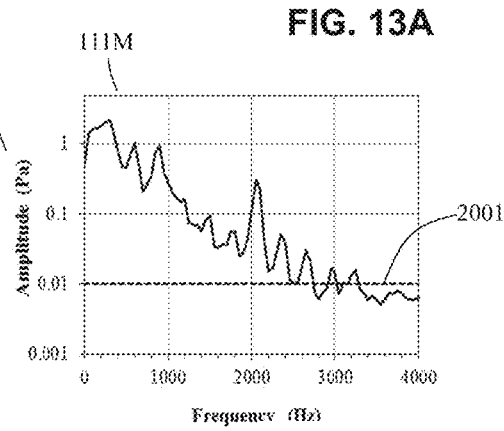
Figure 13D:
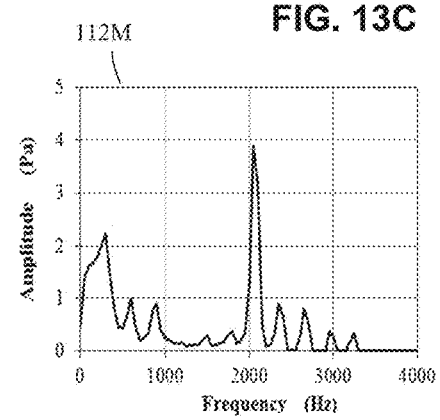
Figure 13E:
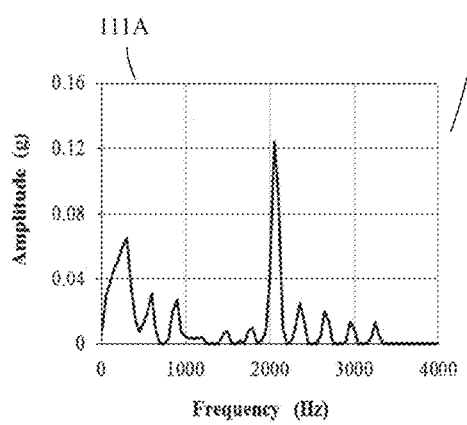
Figure 14A:
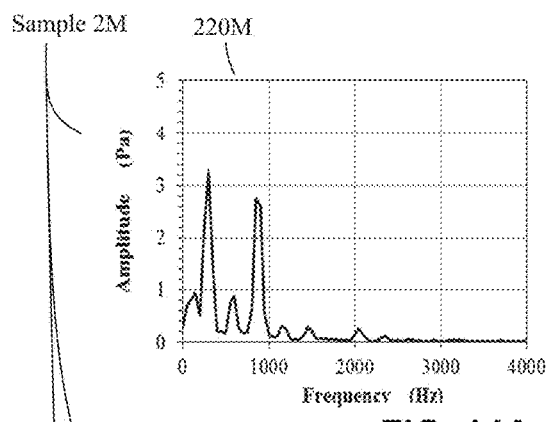
FIGS. 14A-14E are a set of graphs showing raw microphone and accelerometer FFT sample data and filtered and/or restored results for a pair of samples recorded by a microphone and an accelerometer, respectively, on an identical time frame of the sound, according to an embodiment of the invention.
Figure 14B:
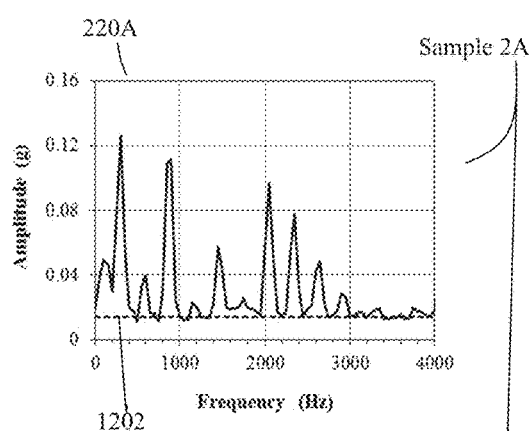
Figure 14C:
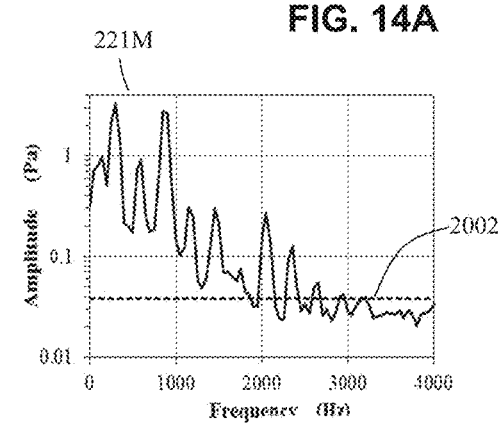
Figure 14D:
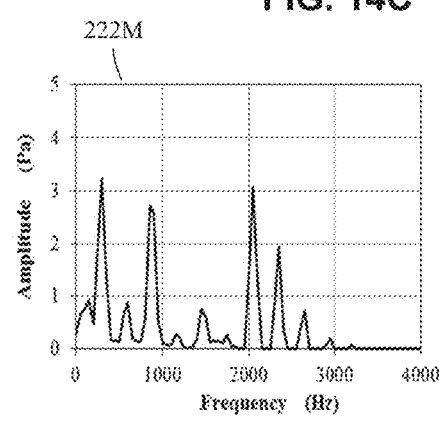
Figure 14E:
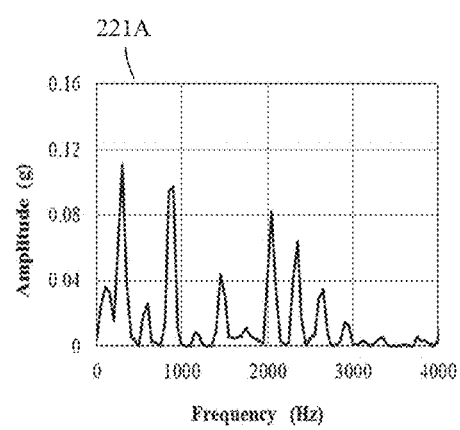

The next step 910 is to build a proper "Gain Function" or select a pre-built one from the Database 990. For example, the graph 100M in FIG. 12 is an exemplary Gain Function found to be satisfactory when applied to the microphone record of this example. Within the frequency range, 1200-2800 Hz (at 1010), for this particular function, the Gain is a power function of frequency.

As like most of functions, there may be some parameters in the Gain Function. Step 920 calls for adjusting the Gain Function parameters. When these parameters are initially adjusted, the result is an initial Restoring Processor 930 composed of Equation (5) and Gain Function (Equation 6). Thereafter, each sample within the Representative Cleaned FFT Data 431 is processed by using an initial Restoring Processor 930 to produce Restored FFT Data 940.

The Restored FFT Data 940 is then examined at the step 700. The Examination 700 is detailed in FIG. 9, but with a substitution of the Cleaned FFT Data 710 in FIG. 9 for the Restored FFT Data 940 in FIG. 11. The Restored FFT Data 940 is either directly examined at the step 720 by comparing each of its sample against the correspondent one of the Representative Cleaned FFT Data 431, and/or transformed into Time Domain Data 732 by the Inverse Fast Fourier Transformation 731. The Time Domain Data 732 can be played back by a Listening Device 733, and the Sound 734 can be examined at step 735.

After examination, a judgment is made at step 950 to conclude whether or not the Restoring Processor 930 is acceptable. If it is not acceptable, the procedure is repeated from the step 910. If otherwise considered acceptable, the Restoring Processor 930, at step 960, is tested with some new cleaned FFT data. Note, the step 960 procedure for "Test Restoring Processor on New Cleaned FFT Data" is essentially identical to that of the examination with the Representative Cleaned FFT Data 431; accomplished by performing steps 930 to 700.

After examination, a judgment is made at step 970 to conclude if the Restoring Processor 930 is still considered acceptable. If it is not acceptable, the procedure is repeated beginning at step 910. If it is acceptable, then the Restoring Processor 930 is decided or otherwise determined and tuned, and can be applied to process the entire record.

After the Restoring Processor 930 is tested and accepted, if the Gain Function is newly created (step 980), it is stored (step 985) in the Gain Function Database 990 for future use.

A Test with Real Data of the Example Records. An exemplary embodiment of the invention was applied to the example records, identified previously, to test principles and methods described herein. Because the signals recorded by the accelerometer can be considered to not be attenuated, and the signals recorded by the microphone are considered to be attenuated, the signals from the microphone were compared against the correspondent signals from the accelerometer to identify the amount of actual attenuation. The accelerometer record was filtered only and the microphone record was firstly filtered and then the attenuation was restored.

For purposes of the test, 30 out of the 51,400 samples in the microphone record and accelerometer record were used to tune the Dynamic Filters and to build a Gain Function (Equation 6). An example describing tuning of the Dynamic Filter was discussed previously. A Gain Function was successfully built using the procedure defined in FIG. 11. The built Gain Function is shown in FIG. 12. With the Tuned Dynamic Filter 640 and the Restoring Processor 930, a methodology according to an exemplary embodiment of the invention was applied to process the records. The results are shown in FIGS. 13A-17B for some representative samples.

FIGS. 13A-13E show the raw FFT sample data and the filtered and restored results for samples 1M and 1A recorded by the microphone and accelerometer, respectively, during an identical time frame of the sound. The raw FFT sample data is indicated by spectrums 110M and 110A in FIGS. 13A and 13B, respectively. Spectrum 111M (FIG. 13C) is the same spectrum as 110M, but with a logarithmic vertical axis. Lines 2001 (FIG. 13C) and 1102 (FIG. 13B) are the evaluated Dynamic Amplitude Noise Cutoff for spectrums 110M and 110A, respectively. Spectrum 112M (FIG. 13D) is the processed result of 110M after filtering and restoration. Spectrum 111A (FIG. 13E) is the processed result of 110A after filtering. A comparison between 110M (FIG. 13A) and 112M (FIG. 13D), 110A (FIG. 13B) and 111A (FIG. 13E) shows that the background noise has been effectively and optimally removed after filtering. The amplitude spectrum of 112M is almost the same as that of 111A, this means that not only was the background noise of 110M effectively and optimally removed, but also the attenuated high frequency components were properly restored.

FIGS. 14A-14E show raw FFT sample data and the filtered and restored results for samples 2M and 2A recorded by the microphone and accelerometer, respectively, on an identical time frame of the sound. Spectrums 220M and 220A illustrate the raw FFT sample data. Spectrum 221M is the same spectrum as 220M, but with a logarithmic vertical axis. Lines 2002 and 1202 indicate the evaluated Dynamic Amplitude Noise Cutoff for 220M and 220A, respectively. Spectrum 222M is the processed result of 220M after filtering and restoration. Spectrum 221A is the processed result of 220A after filtering. A comparison between 220A and 221A shows that the background noise has been effectively and optimally removed after filtering. As discussed before, for the microphone record used in the example, the components of the amplitude spectrum recorded by the microphone with the frequency greater than 3500 Hz attenuated down to the same level as background noise. Therefore, only the components with the frequency less than 3500 Hz can be restored. A comparison between spectrums 222M (FIG. 14D) and 221A (FIG. 14E) show that the amplitude spectrum of 222M is almost same as that of 221A before 3500 Hz. This means that, not only was the background noise of 220M effectively and optimally removed, but also the restorable attenuated high frequency components was properly restored.

FIGS. 15A-15D show the comparison between the processed results using the exemplary dynamic amplitude noise cutoff process described herein, and the conventional constant amplitude noise cutoff methodology for two samples. Amplitude spectrum 112M (FIG. 15A) is the filtered and restored spectra for sample 1M in FIG. 13A, processed using the exemplary Dynamic Amplitude Noise Cutoff process. Spectrum 113M (FIG. 15C) is the filtered and restored spectra for sample 1M using the constant noise cutoff process. Amplitude spectrum 222M (FIG. 15B) is the filtered and restored spectra for sample 2M in FIG. 14A, processed using the exemplary process. Spectrum 223M (FIG. 15D) is the filtered and restored spectra for sample 2M using the constant noise cutoff process. The constant noise cutoff for these two samples is the cutoff located at 2000 in FIGS. 4B and 4D.

Figure 15A:
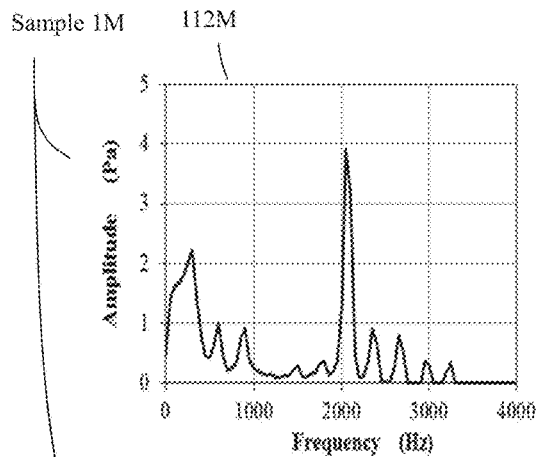
FIGS. 15A-15D are a set of graphs showing a comparison between the processed results using an exemplary dynamic amplitude noise cut off process described herein, according to an embodiment of the invention, and a conventional constant amplitude noise cutoff methodology for two samples.
Figure 15B:
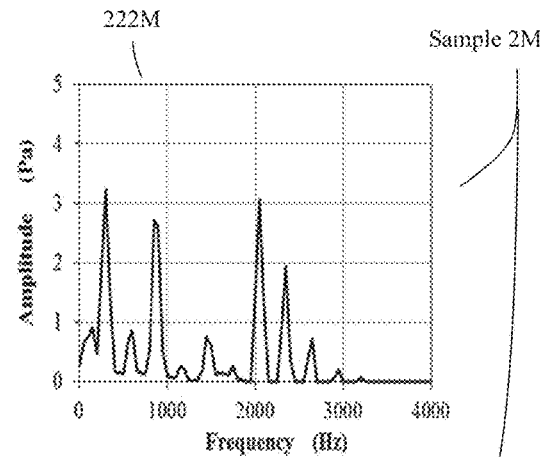
Figure 15C:
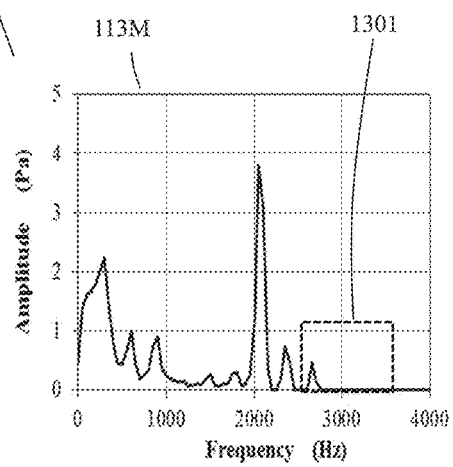

As shown at 1301 by the resultant amplitude spectrum 113M in the FIG. 15C, because the two peaks 1005 and 1006 (FIG. 4B) on the amplitude spectrum diagram 111M of the sample 1M are below the constant cutoff 2000 (FIGS. 4B, 4D), these two peaks were removed when the constant cutoff was applied. Also another peak just before the two removed peaks within the dashed rectangle at 1301 was also seriously suppressed when compared with the spectrum 112M (FIG. 15A) processed using the exemplary Dynamic Amplitude Noise Cutoff process.

Figure 15D:
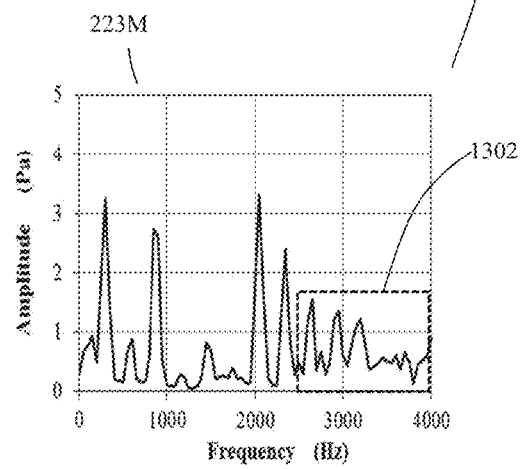

In spectrum 221M (FIG. 4D), the background noise 2003 is above the constant noise cutoff 2000 (FIG. 4D). Therefore, the background noise will not be effectively filtered, i.e., were under filtered. As the result, the under filtered noise were enlarged during the restoration procedure, as shown by the overly restored peaks and under filtered and enlarged noise 1302 on the spectrum 223M (FIG. 15D).

Figures 16A, 16B:
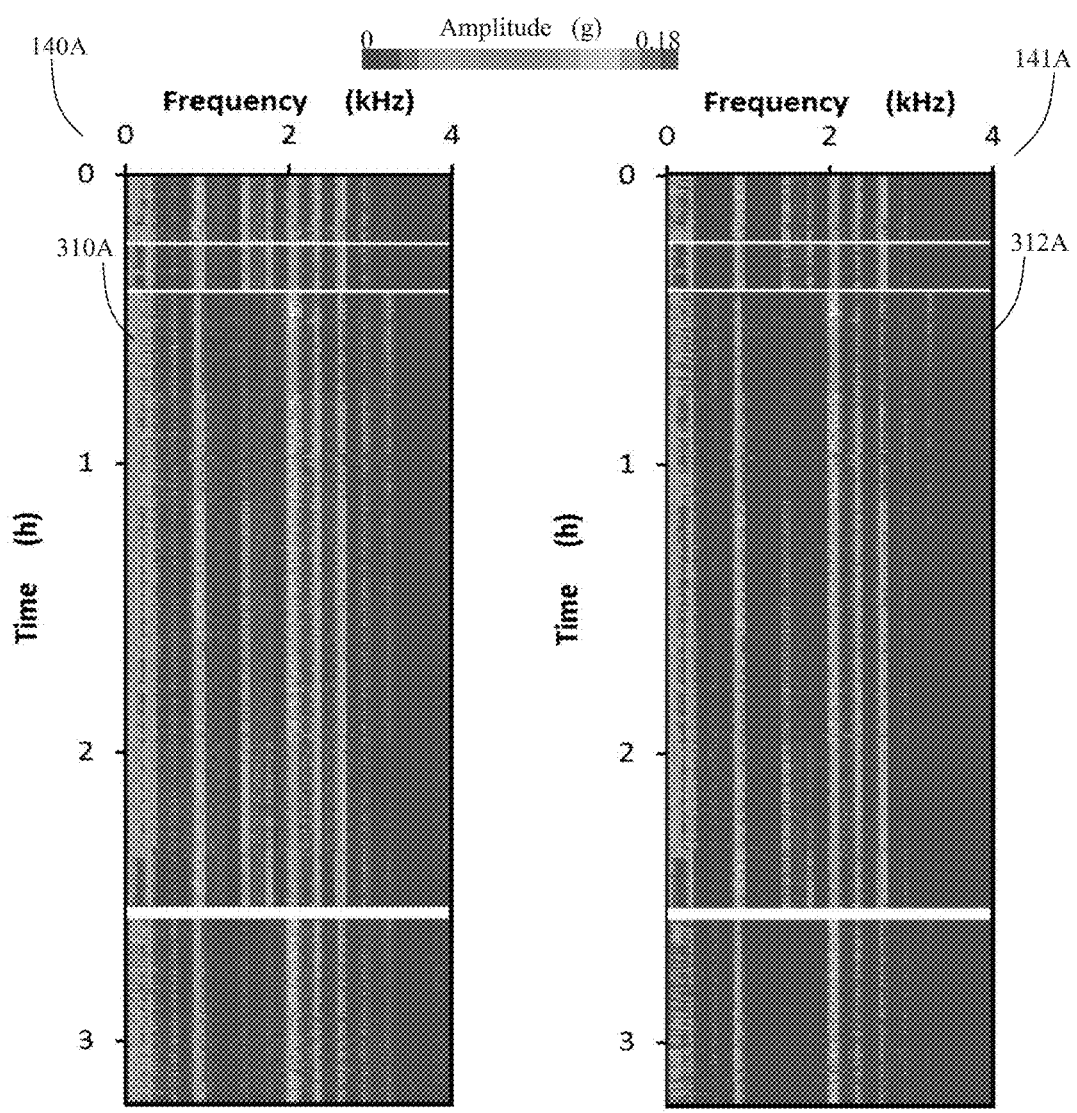
FIGS. 16A-16B are a set of graphs showing raw data comprised of multiple samples and the filtered result, respectively, for part of the accelerometer record, according to an embodiment of the invention.

FIGS. 16A-16B shows raw data 140A (multiple samples) and the filtered result 141A, respectively, for part of the accelerometer record. This part of the record covers the record period of over three hours and is composed of 2300 samples. The vertical axis is time of sample, and the horizontal axis is the frequencies of the sample. The amplitude value of each frequency is represented by the color scheme. The amplitude spectrum of each sample, as represented by 310A for the raw sample data and 312A for the filtered result, is plot on a narrow horizontal frequency band.

Amplitude spectrum diagrams 140A and 141A are the result of all of the samples being plot together consecutively along the time axis. That is, diagrams 140A and 141A are the amplitude spectrum for the group of samples, horizontal lines 310A and 312A are the amplitude spectrum for the individual samples. Comparison between the raw amplitude spectrum 140A and the filtered one 141A shows that the blur (background noise) of the raw data 140A was effectively and optimally removed and the filtered amplitude spectrum diagram 141A is much cleaner.

Figure 17A:
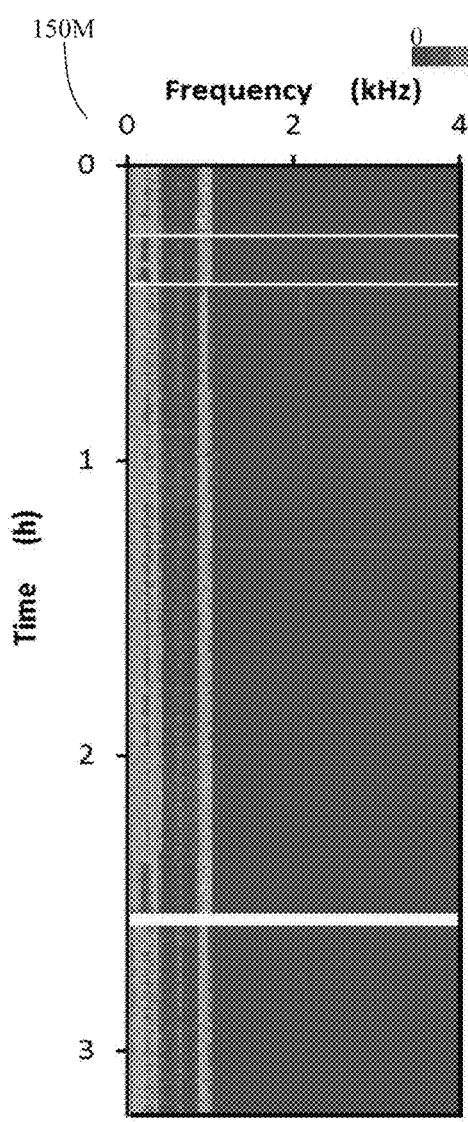
FIGS. 17A and 17B are a set of graphs showing the raw data comprised of multiple samples and filtered and restored results respectively, for part of the microphone record, according to an embodiment of the invention.
Figure 17B:
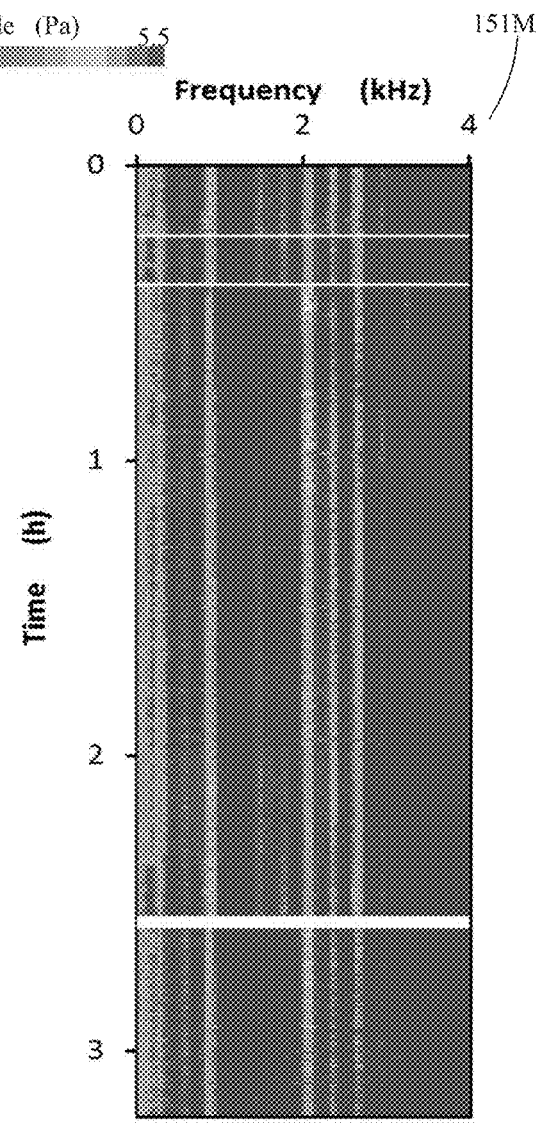

FIGS. 17A and 17B show the raw data 150M and filtered and restored result 151M, respectively, for part of the microphone record using an exemplary embodiment of the invention. The record time period is the same as the record time period in the FIGS. 16A and 16B. That is, both FIGS. 16A and 17A are records of the same sound samples, but recorded by different devices. The high frequency components of the microphone record attenuate significantly. A comparison between the spectrum diagram 140A in the FIG. 16A and spectrum diagram 150M in the FIG. 17A shows that most high frequency (>1500 Hz) components of the microphone record attenuate too low to be recognized. After filtering and restoration, these extremely attenuated high frequency components, however, were well restored, as shown in spectrum diagram 151M (FIG. 17B). The filtered and restored spectrum of the microphone record 151M (FIG. 17B) is almost the same as that of the filtered one of the accelerometer record 141A (FIG. 16B). This proves that the invention disclosed works very effectively and satisfactorily.

In summary, the examples shown in FIGS. 13A-17B demonstrate that the principles, processes and procedures, according to one or more exemplary embodiments of the invention, have the ability to filter out background noise effectively and optimally, and to restore the attenuated high frequency components nearly to their true values.

It is important to note that while embodiments of the present invention have been described in the context of a fully functional system/apparatus, those skilled in the art will appreciate that the mechanism of at least portions of the present invention and/or aspects thereof are capable of being distributed in the form of a non-transitory computer readable medium storing/containing or otherwise embodying instructions in a variety of forms for execution on one or more processors, or the like, and that embodiments of the present invention apply equally regardless of the particular type of media used to actually carry out the distribution. Non-transitory computer readable medium or media which is understood to mean includes all forms of computer readable storage media that do not fall under the category of being non-statutory subject matter, in general, or take the form of a propagating signal per se, in particular. Examples of the non-transitory computer readable media include but are not limited to: nonvolatile, hard-coded type media such as read only memories (ROMs), CD-ROMs, and DVD-ROMs, or erasable, electrically programmable read only memories (EEPROMs), recordable type media such as floppy disks, hard disk drives, CD-R/RWs, DVD-RAMs, DVD-R/RWs, DVD+R/RWs, HD-DVDs, memory sticks, mini disks, laser disks, Blu-ray disks, flash drives, and other newer types of memories, and in certain circumstances, transmission type media such as digital and analog communication links capable of storing/containing or otherwise embodying the instructions, to the exclusion of a propagating signal per se. For example, such media can store or otherwise contain both operating instructions and operations instructions related to the operations associated with computer program/program code 51 and the method steps, described above.

This application is a non-provisional of and claims priority to and the benefit of U.S. Provisional Application No. 61/877,117, filed on Sep. 12, 2013, titled "Dynamic Threshold Methods, Systems, and Program Code for Filtering Noise and Restoring Attenuated High-Frequency Components of Acoustic Signals," and PCT Application PCT/US2014/55516, titled "Dynamic Threshold Methods, Systems, Computer Readable Media, and Program Code For Filtering Noise and Restoring Attenuated High-Frequency Components of Acoustic Signals, filed on Sep. 12, 2014, and is related to U.S. Non-Provisional patent application Ser. No. 14/485,562, titled "Dynamic Threshold Methods For Filtering Noise and Restoring Attenuated High-Frequency Components of Acoustic Signals, filed on Sep. 12, 2014, each incorporated herein by reference in their entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

The invention claimed is:

1. A system comprising:
an acoustic sensor affixed to a metal adapter attached to a machine; and
non-transitory computer readable medium having processor readable code embodied thereon to provide for filtering noise, restoring attenuated spectral components, or both filtering noise and restoring attenuated spectral components in acoustic signals, the processor readable code comprising a set of instructions, that when executed by one or more processors, cause the one or more processors to perform operations comprising:
recording, via the acoustic sensor affixed to the metal adapter attached to the machine, acoustic signal samples, wherein the acoustic signal samples are grouped into one or more acoustic records, and wherein each acoustic record of the one or more acoustic records comprises a subset of the acoustic signal samples in time domain format; and
performing, for each record of one or more acoustic records, the operation of:
transforming the acoustic signal samples of the record from time domain format to frequency domain format to produce a plurality of raw data samples for the record in frequency domain format, wherein each raw data sample of the plurality of raw data samples comprises sample-specific acoustic signal data and sample-specific background noise, and
dynamically filtering each of a plurality of raw data samples in frequency domain format for the respective record to remove or attenuate background noise contained therein to produce a corresponding plurality of cleaned data samples for the respective record, the cleaned data samples for the respective record representing the acoustic signal samples for the respective record with the reduced background noise, the dynamic filtering comprising applying to each raw data sample of the plurality of raw data samples, a record-specific dynamic filter to remove or attenuate the sample-specific background noise of the raw data sample to produce a corresponding plurality of cleaned data samples for the raw data sample, wherein the plurality of cleaned data samples for the respective record comprise the plurality of cleaned data samples for the raw data sample,
the record-specific dynamic filter at least partially being defined by a dynamic amplitude noise cutoff $(A_{th})$,
the dynamic amplitude noise cutoff $(A_{th})$ being defined by a record-specific base noise percentile $(P_b)$ and a record-specific value of a threshold parameter $(C_{th})$,
the record-specific base noise percentile $(P_b)$ being the same for each of the plurality of raw data samples for the respective record,
the threshold parameter value $(C_{th})$ being the same for each of the plurality of raw data samples for the respective record, and
the dynamic amplitude noise cutoff $(A_{th})$ being separately evaluated for and applied to each separate raw data sample of the plurality of raw data samples for the respective record.

2. The system of claim 1, wherein the sample-specific acoustic signal data contained in each separate one of the plurality of cleaned data samples includes substantially attenuated high-frequency components, and wherein the operations further comprise:
restoring the attenuated high-frequency components of the cleaned data samples to thereby produce cleaned and restored data samples being in the frequency domain; and
applying an inverse transformation to convert the cleaned and restored data samples into cleaned and restored data samples in time domain data.

3. The system of claim 1, wherein the sample-specific background noise is time-varying, and wherein the dynamic filter is a tuned dynamic filter, and wherein the operations further comprise: tuning an initial record-specific dynamic filter to form the tuned dynamic filter, the operation of tuning including the operations of:
determining the record-specific Base Noise Percentile for each respective record of the one or more records, the record-specific Base Noise Percentile comprising a $K^{th}$ percentile within a record-specific Specific Frequency Range of an amplitude spectrum of each of the plurality of raw data samples for the respective record, below which each frequency component within the Specific Frequency Range of the respective amplitude spectrum of each of the plurality of raw data samples for the respective record is treated as background noise with substantial certainty; and
determining the record-specific value for the threshold parameter, the record-specific threshold parameter comprising one of the following: a threshold factor to be multiplied with the record-specific base noise percentile and a threshold elevator to be added to the record-specific base noise percentile, to thereby determine a value for the dynamic amplitude noise cutoff to be applied separately to each of the plurality of raw data samples.

4. The system of claim 1, wherein the dynamic filter is a tuned dynamic filter, and wherein the operations further comprise: tuning an initial record-specific dynamic filter, the operation of tuning including the operations of:
   receiving or retrieving a subset of the plurality of raw data samples the respective record of the one or more records;
   selecting a record-specific Specific Frequency Range for the respective record;
   selecting the record-specific Base Noise Percentile for the respective record;
   selecting a value of the record-specific Threshold Parameter for the respective record;
   determining the Dynamic Amplitude Noise Cutoff for the respective record, the Dynamic Amplitude Noise Cutoff defined by the selected Base Noise Percentile and the selected record-specific value of the Threshold Parameter; and
   evaluating results of an initial Dynamic Filter at least partially defined by the Dynamic Amplitude Noise Cutoff, on one or more samples within a set of representative data samples extracted from the plurality of raw data samples to thereby construct the tuned dynamic filter.

5. The system of claim 1, wherein the sample-specific background noise is time-varying, and wherein the dynamic filter is a tuned dynamic filter, and wherein the operations further comprise: tuning an initial record-specific dynamic filter to form the tuned dynamic filter, the operation of tuning including the operations of:
   receiving or retrieving a subset of the plurality of raw data samples for each respective record of the one or more records, wherein:
   if the respective record is a recorded record, performing the operation of retrieving a subset of the plurality of raw data samples recorded at substantially different times with different background noise levels to thereby define a set of Representative FFT Data samples; and
   if the respective record is an online record to be processed and the raw data samples cannot be selected at substantially different times, performing the operation of receiving a subset of the plurality of raw data samples at a beginning of the respective record to thereby define the set of Representative FFT Data samples.

6. The system of claim 1, wherein the sample-specific background noise is time-varying, and wherein the dynamic filter is a tuned dynamic filter, and wherein the operations further comprise: tuning an initial record-specific dynamic filter to form the tuned dynamic filter, the operation of tuning including the operation of:
   selecting a Specific Frequency Range for a respective record of the one or more records, the Specific Frequency Range defined by a range of frequencies common to each sample of a set of Representative FFT Data samples containing frequency components being dominated by background noise, or if no range of frequencies is dominated by background noise, a range of frequencies common to each of the samples of the set of Representative FFT data samples containing a higher percentage of background noise than other substantial ranges of consecutive frequencies of the set of Representative FFT data samples.

7. The system of claim 6, wherein the record-specific Base Noise Percentile is an operational record-specific Base Noise Percentile, and wherein the operations further comprise:
   selecting an initial Base Noise Percentile for the respective record of the one or more records, to include identifying an apparent dividing amplitude under which at least approximately all of the frequency components within the selected Specific Frequency Range are background noise for each of the samples within the set of Representative FFT Data samples.

8. The system of claim 1, wherein the record-specific Base Noise Percentile is an operational record-specific Base Noise Percentile, wherein the dynamic filter is a record-specific tuned dynamic filter, and wherein the operations further comprise: tuning a candidate record-specific dynamic filter to form the record-specific tuned dynamic filter, the operation of tuning including the operation of:
   selecting an initial Base Noise Percentile for a respective record of the one or more records,
   selecting an initial value for the Threshold Parameter for the respective record of the one or more records;
   identifying an initial value for the Threshold Parameter;
   determining an initial Dynamic Amplitude Noise Cutoff, the initial Dynamic Amplitude Noise Cutoff defined by the selected initial Base Noise Percentile and the selected initial value of the Threshold Parameter; and
   evaluating the initial Dynamic Amplitude Noise Cutoff on one or more samples within a set of Representative FFT data samples.

9. The system of claim 8, wherein the raw data samples are raw FFT data samples, wherein the cleaned data samples are Cleaned FFT data samples, and wherein the operation of evaluating the initial Dynamic Amplitude Noise Cutoff on one or more samples within the set of Representative FFT data samples, comprises one or more of the following operations:
   graphically evaluating an amplitude location of the Dynamic Amplitude Noise Cutoff of one or more of the samples within the set of Representative FFT data samples; and
   evaluating results of an initial Dynamic Filter at least partially defined by the initial Dynamic Amplitude Noise Cutoff, on one or more samples within the set of Representative FFT data samples, to include:
   determining the initial Dynamic Filter,
   performing initial dynamic filtering of the one or more samples within the set of Representative FFT data to thereby produce a corresponding one or more of the Cleaned FFT data samples, and
   directly graphically examining the one or more of the Cleaned FFT data samples by comparing each respective cleaned FFT data sample to its corresponding raw FFT data sample to thereby determine if the initial Dynamic Filter is acceptable or if further tuning is required.

10. The system of claim 8, wherein the raw data samples are raw FFT data samples, wherein the cleaned data samples are cleaned FFT data samples, and wherein the operation of evaluating the initial Dynamic Amplitude Noise Cutoff on one or more samples within a set of Representative FFT data samples, comprises the operation of:
   evaluating results of an initial Dynamic Filter at least partially defined by the initial Dynamic Amplitude Noise Cutoff, on one or more samples within the set of Representative FFT data samples, to include:
   determining the initial Dynamic Filter, performing initial dynamic filtering of the one or more samples within the set of Representative FFT data to thereby produce a corresponding one or more Cleaned FFT data samples, and examining one or more time domain data samples corresponding to the one or more Cleaned FFT data samples, to include:

performing an inverse FFT on the one or more cleaned FFT data samples to thereby transform the cleaned FFT data into time domain format to thereby produce the one or more time domain data samples, and producing sounds corresponding to the one or more time domain data samples using a listening device to thereby determine if the initial Dynamic Filter is acceptable or if further tuning is required.

11. The system of claim 8, wherein the operation of evaluating the initial Dynamic Amplitude Noise Cutoff on one or more samples within a set of Representative FFT data samples, comprises the operation of:

evaluating results of an initial Dynamic Filter at least partially defined by the initial Dynamic Amplitude Noise Cutoff, on one or more samples within the set of Representative FFT data samples; and performing one of the following responsive to the operation of evaluating results of the initial Dynamic Filter:

if results of the initial Dynamic Filter are not acceptable, repeating the operations of adjusting the Threshold Factor to thereby shift the Dynamic Amplitude Noise Cutoff in a corrective direction, and evaluating results of the adjusted initial Dynamic Filter, until acceptable, and if results of the evaluation of the initial Dynamic Filter are acceptable, evaluating the initial Dynamic Filter on a second set of Representative FFT data samples.

12. The system of claim 1, wherein the sample-specific acoustic signal data contained in each separate one of the plurality of cleaned data samples includes substantially attenuated high-frequency components, and wherein the operations further comprise:

restoring the attenuated high-frequency components of the cleaned data samples of each respective record of the one or more records to thereby produce cleaned and restored data samples being in the frequency domain, the operation of restoring performed through application of a record-specific Restoring Processor at least partially defined by a portion of the cleaned data samples and a Gain Function.

13. The system of claim 12, wherein the cleaned data samples are cleaned FFT data samples, and wherein the operations further comprise performing one of the following:

if the cleaned FFT data samples are stored such that a subset of the plurality of the cleaned FFT data samples can be selected at substantially different time intervals, retrieving a subset of the plurality of Cleaned FFT data samples representing samples of signals recorded at substantially different times with probable different background noise levels to thereby define a set of Representative Cleaned FFT Data samples used in building or selecting the gain function and forming the record-specific Restoring Processor; and if the cleaned FFT data samples are streamed online such that a subset of the plurality of the cleaned FFT data samples cannot be selected at substantially different time intervals, receiving a subset of the plurality of cleaned FFT data samples at a beginning of the respective record to thereby define the set of Representative Cleaned FFT Data samples used in building or selecting the gain function and forming the restoring Processor.

14. The system of claim 12, wherein the cleaned data samples are cleaned FFT data samples, and wherein the record-specific Restoring Processor is an operational record-specific Restoring Processor, and wherein the operations further comprise:

selecting an initial Restoring Processor for the respective record of the one or more records, to include:

selecting a set of Representative Cleaned FFT data samples from the plurality of cleaned FFT data samples;

building or selecting the gain function from a database responsive to the Representative Cleaned FFT data samples;

adjusting parameters of the gain function to thereby form an initial Restoring Processor;

performing initial restoration processing of the one or more samples within the set of Representative Cleaned FFT data samples by the initial Restoring Process at least partially defined by the gain function, to thereby produce a corresponding one or more restored samples within a set of Restored FFT data samples; and evaluating the initial Restoring Processor.

15. The system of claim 14, further comprising the operation of performing one of the following sets of operations responsive to the operation of evaluating the initial Restoring Processor:

if results of the initial Restoring Processor are not acceptable, repeating the operations of building or selecting a new gain function defining a replacement gain function, adjusting parameters of the replacement gain function to thereby adjust the initial Restoring Processor, and evaluating results of the adjusted initial Restoring Processor, until acceptable; and if results of the evaluation of the initial Restoring Processor are acceptable, evaluating the initial Restoring Processor on a second subset of the plurality of Cleaned FFT data samples.

16. The system of claim 14, wherein the operation of evaluating the initial Restoring Processor comprises the operation of:

graphically comparing each sample of the set of Restored FFT data samples with its correspondent Cleaned FFT data sample.

17. The system of claim 14, wherein the operation of evaluating the initial Restoring Processor comprises the operation of:

examining one or more time domain data samples corresponding to one or more samples of the set of Restored FFT data samples, to include:

performing an inverse FFT on the one or more Restored FFT data samples to thereby transform the Restored FFT data into time domain format to thereby produce the one or more time domain data samples, and producing sounds corresponding to the one or more time domain data samples using a listening device.

18. A system comprising:

an acoustic sensor affixed to a metal adapter to a machine; and non-transitory computer readable medium having processor readable code embodied thereon to provide for filtering noise, restoring attenuated spectral components, or both filtering noise and restoring attenuated spectral components in acoustic signals, the processor readable code comprising a set of instructions, that when executed by one or more processors, cause the one or more processors to perform operations comprising:

recording, via the acoustic sensor affixed to the metal adapter attached to the machine, acoustic signals for a preselected time duration to form one or more records of acoustic signals, the acoustic signals being in the time domain;

for each record of the one or more records:
sampling the acoustic signals within the respective record to thereby form sampled digitized data, the sampled digitized data comprising a plurality of raw data samples being in time domain format, applying a Fast Fourier Transform (FFT) to convert the plurality of raw data samples for the respective record being in time domain format into a plurality of raw FFT data samples being in frequency domain format, each of the raw FFT data samples comprising sample-specific acoustic signal data and sample-specific background noise, the sample-specific acoustic signal data having substantially attenuated high-frequency components, dynamically filtering each of the plurality of raw FFT data samples for the respective record to remove or attenuate background noise contained therein to produce a corresponding plurality of cleaned FFT data samples for the respective record, the cleaned FFT data samples for the respective record representing that acoustic signal samples for the respective record with reduced background noise, the sample-specific background noise of each separated one of the plurality of raw FFT data samples being removed or attenuated by a record-specific dynamic filter applied to each of the plurality of raw FFT data samples to produce the corresponding plurality of cleaned FFT data samples, each of the cleaned FFT data samples comprising the sample-specific acoustic signal data having substantially attenuated high-frequency components, the record-specific dynamic filter at least partially defined by a dynamic amplitude noise cut off, the dynamic amplitude noise cut off defined by:
a record-specific base noise percentile evaluated for each of the plurality of raw FFT data samples, and
a record-specific value of a threshold parameter;

restoring the attenuated high-frequency components of the cleaned data samples to thereby produce cleaned and restored data samples being in the frequency domain, the operation of restoring performed through application of a record-specific Restoring Processor at least partially defined by a portion of the cleaned data samples and a Gain Function; and applying an inverse transformation to convert the cleaned and restored data samples into cleaned and restored data samples in time domain data.

19. The system of claim 18, wherein the sample-specific background noise is time-varying, wherein the dynamic filter is a tuned record-specific dynamic filter, and wherein the operations further comprise: tuning an initial record-specific dynamic filter to form the tuned record-specific dynamic filter, the operation of tuning including performing the following operations for each of the one or more records:

determining the record-specific Base Noise Percentile comprising a $K^{th}$ percentile within a record-specific Specific Frequency Range of an amplitude spectrum of each of the plurality of raw data samples for the respective record, below which each frequency component within the Specific Frequency Range of the respective amplitude spectrum of each of the plurality of raw data samples within the respective record is treated as background noise with substantial certainty; and determining the record-specific value for the threshold parameter, the record-specific threshold parameter comprising one of the following:
a threshold factor to be multiplied with the record-specific base noise percentile to determine a value for the dynamic amplitude noise cutoff to be applied separately to each of the plurality of raw data samples, and
a threshold elevator to be added to the record-specific base noise percentile to determine the value for the dynamic amplitude noise cutoff to be applied separately to each of the plurality of raw data samples.

20. The system of claim 18, wherein the dynamic filter is a tuned dynamic filter, and wherein the operations further comprise: tuning the record-specific dynamic filter, the operation of tuning including the operations of:

receiving or retrieving a subset of the plurality of raw data samples for each respective record of the one or more records, wherein:
if the respective record is a recorded record, performing the operation of retrieving a subset of the plurality of raw data samples recorded at substantially different times with different background noise levels to thereby define a set of Representative FFT Data samples, and
if the respective record is an online record to be processed and the raw data samples cannot be selected at substantially different times, performing the operation of receiving a subset of the plurality of raw data samples at a beginning of the respective record to thereby define the set of Representative FFT Data samples;

selecting a Specific Frequency Range for a respective record of the one or more records, the Specific Frequency Range defined by a range of frequencies common to each sample of a set of Representative FFT Data samples containing frequency components being dominated by background noise, or if no range of frequencies is dominated by background noise, a range of frequencies common to each of the samples of the set of Representative FFT data samples containing a higher percentage of background noise than other substantial ranges of consecutive frequencies of the set of Representative FFT data samples;

selecting an initial Base Noise Percentile for the respective record of the one or more records, to include identifying an apparent dividing amplitude under which at least approximately all of the frequency components within the selected Specific Frequency Range are background noise for each of the samples within the set of Representative FFT Data samples;

selecting an initial value of the record-specific Threshold Parameter for the respective record;

determining the Dynamic Amplitude Noise Cutoff for the respective record, the Dynamic Amplitude Noise Cutoff defined by the selected Base Noise Percentile and the selected record-specific value of the Threshold Parameter; and evaluating results of the initial Dynamic Filter at least partially defined by the Dynamic Amplitude Noise Cutoff, on one or more samples within a set of Representative data samples extracted from the plurality of raw data samples to thereby construct the tuned dynamic filter.

21. The system of claim 20, wherein the operation of evaluating the initial Dynamic Filter on one or more samples within the set of Representative FFT data samples, comprises one or more of the following operations:
graphically evaluating an amplitude location of the Dynamic Amplitude Noise Cutoff of one or more of the samples within the set of Representative FFT data samples; and
evaluating results of an initial Dynamic Filter at least partially defined by the initial Dynamic Amplitude Noise Cutoff, on one or more samples within the set of Representative FFT data samples, to include:
determining the initial Dynamic Filter,
performing initial dynamic filtering of the one or more samples within the set of Representative FFT data to thereby produce a corresponding one or more Cleaned FFT data samples, and
directly graphically examining the one or more Cleaned FFT data samples by comparing each respective cleaned FFT data sample to its corresponding raw FFT data sample to thereby determine if the initial Dynamic Filter is acceptable or if further tuning is required;
if results of the initial Dynamic Filter are not acceptable, repeating the operations of adjusting the Threshold Factor to shift the Dynamic Amplitude Noise Cutoff in a corrective direction resulting in an adjusted initial Dynamic Filter, and evaluating results of the adjusted initial Dynamic Filter, until acceptable; and
if the results of the evaluation of the initial Dynamic Filter are acceptable, evaluating the initial Dynamic Filter on a second set of Representative FFT data samples.

22. The system of claim 20, wherein the raw data samples are raw FFT data samples, wherein the cleaned data samples are cleaned FFT data samples, and wherein the operation of evaluating the initial Dynamic Amplitude Noise Cutoff on one or more samples within a set of Representative FFT data samples, comprises the operation of:
evaluating results of an initial Dynamic Filter at least partially defined by the initial Dynamic Amplitude Noise Cutoff, on one or more samples within the set of Representative FFT data samples, to include:
determining the initial Dynamic Filter,
performing initial dynamic filtering of the one or more samples within the set of Representative FFT data to thereby produce a corresponding one or more Cleaned FFT data samples, and
examining one or more time domain data samples corresponding to the one or more cleaned FFT data samples, to include:
performing an inverse FFT on the one or more cleaned FFT data samples to thereby transform the cleaned FFT data into time domain format to thereby produce the one or more time domain data samples, and
producing sounds corresponding to the one or more time domain data samples using a listening device to thereby determine if the initial Dynamic Filter is acceptable or if further tuning is required;
if results of the initial Dynamic Filter are not acceptable, repeating the operations of adjusting the Threshold Factor to thereby shift the Dynamic Amplitude Noise Cutoff in a corrective direction and evaluating results of a replacement initial Dynamic Filter, until acceptable; and
if results of the evaluation of the initial Dynamic Filter are acceptable, evaluating the initial Dynamic Filter on a second set of Representative FFT data samples.

23. The system of claim 18, further comprising the operation of performing one of the following sets of operations:
if the cleaned FFT data samples are stored such that a subset of the plurality of the cleaned FFT data samples can be selected at substantially different time intervals, performing the operation of retrieving a subset of the plurality of Cleaned FFT data samples representing samples of signals recorded at substantially different times with probable different background noise levels to thereby define a set of Representative Cleaned FFT Data samples used in building or selecting the gain function and forming the record-specific Restoring Processor; and
if the cleaned FFT data samples are streamed online such that a subset of the plurality of the cleaned FFT data samples cannot be selected at substantially different time intervals, performing the operation of receiving a subset of the plurality of Cleaned FFT data samples at a beginning of the respective record to thereby define the set of Representative Cleaned FFT Data samples used in building or selecting the gain function and forming the record-specific Restoring Processor.

24. The system of claim 18, wherein the record-specific Restoring Processor is an operational record-specific Restoring Processor, and wherein the operations further comprise:
selecting an initial Restoring Processor for the respective record of the one or more records, to include:
selecting a set of Representative Cleaned FFT data samples from the plurality of cleaned FFT data samples;
building or selecting the gain function from a database responsive to the Representative Cleaned FFT data samples;
adjusting parameters of the gain function to thereby form an initial Restoring Processor;
performing initial restoration processing of the one or more samples within the set of Representative Cleaned FFT data samples by the initial Restoring Process at least partially defined by the gain function, to thereby produce a corresponding one or more restored samples within a set of Restored FFT data samples;
evaluating the initial Restoring Processor; and
performing one of the following sets of operations responsive to the operation of evaluating the initial Restoring Processor:
if results of the initial Restoring Processor are not acceptable, repeating the operations of building or selecting a new gain function defining a replacement gain function, adjusting parameters of the replacement gain function, and evaluating results of a replacement initial Restoring Processor, until acceptable, and
if results of the evaluation of the initial Restoring Processor are acceptable, evaluating the initial Restoring Processor on a second subset of the plurality of Cleaned FFT data samples.

25. The system of claim 24, wherein the operation of evaluating the initial Restoring Processor comprises one or more the following operations:

graphically comparing each sample of the set of Restored FFT data samples with its correspondent Cleaned FFT data sample; and examining one or more time domain data samples corresponding to one or more samples of the set of Restored FFT data samples, to include: performing an inverse FFT on the one or more Restored FFT data samples to thereby transform the Restored FFT data into time domain format to thereby produce the one or more time domain data samples, and producing sounds corresponding to the one or more time domain data samples using a listening device.

26. A system comprising:

an acoustic sensor affixed to a metal adapter attached to a machine; and non-transitory computer readable medium having processor readable code embodied thereon to provide for filtering noise, restoring attenuated spectral components, or both filtering noise and restoring attenuated spectral components in acoustic signals, the processor readable code comprising a set of instructions, that when executed by one or more processors, cause the one or more processors to perform operations comprising:

recording, via the acoustic sensor affixed to the metal adapter attached to the machine, acoustic signals for a preselected time duration to form one or more records of acoustic signals, the acoustic signals being in the time domain; and for each record of the one or more records:

sampling the acoustic signals within the respective record to thereby form sampled digitized data, the sampled digitized data comprising a plurality of raw data samples being in time domain format, applying a Fast Fourier Transform (FFT) to convert the plurality of raw data samples for the respective record being in time domain format into a plurality of raw FFT data samples being in frequency domain format, each of the raw FFT data samples comprising sample-specific acoustic signal data and sample-specific background noise varying between raw FFT data samples for the respective record, the sample-specific acoustic signal data having substantially attenuated high-frequency components, tuning an initial record-specific dynamic filter at least partially defined by an initial dynamic amplitude noise cut off defined by an initial record-specific base noise percentile and an initial record-specific value of a threshold parameter to form a tuned record-specific dynamic filter for application to each raw FFT data sample of the plurality of raw data samples, to include:

determining the initial record-specific Base Noise Percentile, the initial record-specific Base Noise Percentile comprising a $K^{th}$ percentile within a record-specific Specific Frequency Range of an amplitude spectrum of each of the plurality of raw FFT data samples of the respective record, below which each frequency component within the Specific Frequency Range of the respective amplitude spectrum of each of the plurality of raw FFT data samples for the respective record is treated as background noise with substantial certainty, and determining the initial record-specific value for the threshold parameter, the initial record-specific threshold parameter comprising one of the following:

a threshold factor to be multiplied with the initial record-specific base noise percentile to determine a value for a selected dynamic amplitude noise cutoff to be applied separately to each of the plurality of raw FFT data samples, and a threshold elevator to be added to the initial record-specific base noise percentile to determine the value for a selected dynamic amplitude noise cutoff to be applied separately to each of the plurality of raw FFT data samples, dynamically filtering each of the plurality of raw FFT data samples for the respective record to remove or attenuate background noise contained therein to produce a corresponding plurality of cleaned FFT data samples for the respective record, the cleaned FFT data samples for the respective record representing the acoustic signal samples for the respective record with reduced background noise, the sample-specific background noise removed or attenuated by the tuned record-specific dynamic filter to produce the corresponding cleaned FFT data samples, the cleaned FFT data samples comprising the sample-specific acoustic signal data having substantially attenuated high-frequency components, the tuned record-specific dynamic filter at least partially defined by the selected dynamic amplitude noise cut off applied to each of the plurality of raw FFT data samples, the selected dynamic amplitude noise cut off defined by: a selected value of the record-specific base noise percentile, and a selected record-specific value of the threshold parameter, restoring the attenuated high-frequency components of the cleaned data samples to thereby produce cleaned and restored data samples being in the frequency domain, the operation of restoring performed through application of a record-specific Restoring Processor at least partially defined by a portion of the cleaned data samples and a Gain Function, and applying an inverse transformation to convert the cleaned and restored data samples into cleaned and restored data samples in time domain data.

27. A system to provide for filtering noise, restoring attenuated spectral components, or both filtering noise and restoring attenuated spectral components in acoustic signals, the system comprising:

an acoustic sensor affixed to a metal adapter attached to a machine;

a dynamic noise filtering and signal restoration computer having one or more processors and memory in communication with the one or more processors; and a dynamic noise filtering and signal restoration program stored in the memory of the dynamic noise filtering and signal restoration computer to provide for filtering noise, restoring attenuated spectral components or both filtering noise and restoring attenuated spectral components in acoustic signals, the program including instructions that when executed by the dynamic noise filtering and signal restoration computer cause the computer to perform the operations of:

recording, via the acoustic sensor affixed to the metal adapter attached to the machine, acoustic signals for a preselected time duration to form one or more records of acoustic signals, the acoustic signals being in the time domain;

for each record of the one or more records:

sampling the acoustic signals within the respective record to thereby form sampled digitized data, the sampled digitized data comprising a plurality of raw data samples being in time domain format, applying a Fast Fourier Transform (FFT) to convert the plurality of raw data samples for the respective record being in time domain format into a plurality of raw FFT data samples being in frequency domain format, each of the raw FFT data samples comprising sample-specific acoustic signal data and sample-specific background noise, the sample-specific acoustic signal data having substantially attenuated high-frequency components, dynamically filtering each of the plurality of raw FFT data samples for the respective record to remove or attenuate background noise contained therein to produce a corresponding plurality of cleaned FFT data samples for the respective record, the cleaned FFT data samples for the respective record representing the acoustic signal sample for the respective record with reduced background noise, the sample-specific background noise of each separated one of the plurality of raw FFT data samples being removed or attenuated by a record-specific dynamic filter applied to each of the plurality of raw FFT data samples to produce the corresponding plurality of cleaned FFT data samples, each of the cleaned FFT data samples comprising the sample-specific acoustic signal data having substantially attenuated high-frequency components, the record-specific dynamic filter at least partially defined by a dynamic amplitude noise cut off, the dynamic amplitude noise cut off defined by:
a record-specific base noise percentile evaluated for each of the plurality of raw FFT data samples, and
a record-specific value of a threshold parameter;

restoring the attenuated high-frequency components of the cleaned data samples to thereby produce cleaned and restored data samples being in the frequency domain, the operation of restoring performed through application of a record-specific Restoring Processor at least partially defined by a portion of the cleaned data samples and a Gain Function; and applying an inverse transformation to convert the cleaned and restored data samples into cleaned and restored data samples in time domain data.

28. A system to provide for filtering noise, restoring attenuated spectral components, or both filtering noise and restoring attenuated spectral components in acoustic signals, the system comprising:

an acoustic sensor affixed to a metal adapter attached to machine, and a dynamic noise filtering and signal restoration computer having one or more processors and memory in communication with the one or more processors; and a dynamic noise filtering and signal restoration program stored in the memory of the dynamic noise filtering and signal restoration computer to provide for filtering noise, restoring attenuated spectral components or both filtering noise and restoring attenuated spectral components in acoustic signals, the program including instructions that when executed by the dynamic noise filtering and signal restoration computer cause the computer to perform the operations of:

recording, via the acoustic sensor affixed to the metal adapter attached to the machine, acoustic signals for a preselected time duration to form one or more records of acoustic signals, the acoustic signals being in the time domain; and for each record of the one or more records:
sampling the acoustic signals within the respective record to thereby form sampled digitized data, the sampled digitized data comprising a plurality of raw data samples being in time domain format, applying a Fast Fourier Transform (FFT) to convert the plurality of raw data samples for the respective record being in time domain format into a plurality of raw FFT data samples being in frequency domain format, each of the raw FFT data samples comprising sample-specific acoustic signal data and sample-specific background noise varying between raw FFT data samples for the respective record, the sample-specific acoustic signal data having substantially attenuated high-frequency components, tuning an initial record-specific dynamic filter at least partially defined by an initial dynamic amplitude noise cut off defined by an initial record-specific base noise percentile and an initial record-specific value of a threshold parameter to form a tuned record-specific dynamic filter for application to each raw FFT data sample of the plurality of raw data samples, to include:

determining the initial record-specific Base Noise Percentile, the initial record-specific Base Noise Percentile comprising a $K^{th}$ percentile within a record-specific Specific Frequency Range of an amplitude spectrum of each of the plurality of raw FFT data samples of the respective record, below which each frequency component within the Specific Frequency Range of the respective amplitude spectrum of each of the plurality of raw FFT data samples for the respective record is treated as background noise with substantial certainty, and determining the initial record-specific value for the threshold parameter, the initial record-specific threshold parameter comprising one of the following:

a threshold factor to be multiplied with the initial record-specific base noise percentile to determine a value for a selected dynamic amplitude noise cutoff to be applied separately to each of the plurality of raw FFT data samples, and a threshold elevator to be added to the initial record-specific base noise percentile to determine the value for a selected dynamic amplitude noise cutoff to be applied separately to each of the plurality of raw FFT data samples, dynamically filtering each of the plurality of raw FFT data samples for the respective record to remove or attenuate background noise contained therein to produce a corresponding plurality of cleaned FFT data samples for the respective record, the cleaned FFT data samples for the respective record representing the acoustic signal samples for the respective record with reduced background noise, the sample-specific background noise removed or attenuated by the tuned record-specific dynamic filter to produce the corresponding cleaned FFT data samples, the cleaned FFT data samples comprising the sample-specific acoustic signal data having substantially attenuated high-frequency components, the tuned record-specific dynamic filter at least partially defined by the selected dynamic amplitude noise cut off applied to each of the plurality of raw FFT data samples, the selected dynamic amplitude noise cut off defined by: a selected value of the record-specific base noise percentile, and a selected record-specific value of the threshold parameter, restoring the attenuated high-frequency components of the cleaned data samples to thereby produce cleaned and restored data samples being in the frequency domain, the operation of restoring performed through application of a record-specific Restoring Processor at least partially defined by a portion of the cleaned data samples and a Gain Function, and applying an inverse transformation to convert the cleaned and restored data samples into cleaned and restored data samples in time domain data.

* * * * *

UNITED STATES PATENT AND TRADEMARK OFFICE
CERTIFICATE OF CORRECTION

PATENT NO. : 9,696,444 B2
APPLICATION NO. : 14/485613
DATED : July 4, 2017
INVENTOR(S) : Yunlai Yang It is certified that error appears in the above-identified patent and that said Letters Patent is hereby corrected as shown below:

In the Claims

In Column 26, Line 4, Claim 1, after the phrase "respective record with" please delete the word "the"
In Column 30, Line 61, Claim 18, after the word "adapter" please add the word --attached--
In Column 31, Line 30, Claim 18, please delete the word "that" and replace with the word --the--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*